(12) United States Patent
Kumar et al.

(10) Patent No.: US 11,510,639 B2
(45) Date of Patent: Nov. 29, 2022

(54) SYSTEMS AND METHODS FOR A MOBILE IMAGING SYSTEM

(71) Applicant: GE Precision Healthcare LLC, Milwaukee, WI (US)

(72) Inventors: G. S. Sampath Kumar, Hosur (IN); Abhishek Chetty, Bangalore (IN); Christopher Jablonowski, Hartland, WI (US); Stephen Paul Schroeder, Waukesha, WI (US); Ashis Mandal, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 93 days.

(21) Appl. No.: 17/306,722

(22) Filed: May 3, 2021

(65) Prior Publication Data
US 2022/0346735 A1 Nov. 3, 2022

(51) Int. Cl.
*A61B 6/00* (2006.01)

(52) U.S. Cl.
CPC .................. *A61B 6/4405* (2013.01)

(58) Field of Classification Search
CPC .................................................. A61B 6/4405
See application file for complete search history.

(56) References Cited

U.S. PATENT DOCUMENTS

2011/0249807 A1* 10/2011 Dirisio ................... A61B 6/447
378/198

OTHER PUBLICATIONS

"DX-D 100 Mobile DR with FreeView Technology—Taking mobile imaging to the next level," Hitachi Website, Available Online at https://www.hitachihealthcare.com/analytics_popup.html?url=/sites/default/files/downloads/AGFA%20DX-D%20100%20Freeview%20Brochure_0.pdf, Available as Early as Jan. 2015, 4 pages.

* cited by examiner

*Primary Examiner* — Dani Fox
(74) *Attorney, Agent, or Firm* — McCoy Russell LLP

(57) ABSTRACT

Methods and systems are provided for collapsing a column of a mobile imaging system. In one example, a method may include collapsing a column coupled to a mobile imaging system in response to user interaction, while concomitantly driving the mobile imaging system.

20 Claims, 12 Drawing Sheets

SYSTEMS AND METHODS FOR A MOBILE IMAGING SYSTEM

FIELD

Embodiments of the subject matter disclosed herein relate to enabling collapsing of a column while driving a mobile x-ray system.

BACKGROUND

Mobile imaging systems, such as mobile x-ray devices, are often mounted on motorized mobile drive systems such as carts that are drivable to a patient's location. The cart typically has four wheels, including a pair of wheels that are driven by a motor to move the system. The imaging assembly (such as an x-ray source or tube) may be encased in a horizontal tube arm, which may be mounted on a column proximate the front of the cart.

Mobile imaging systems, such as a mobile x-ray unit, may include an expandable tube arm attached to a column. Additionally, at the end of the tube arm opposite to the column, an imaging assembly, such as an x-ray tube and collimator, may be attached. The tube arm may contain several nested segments, which may extend and contract in a telescoping fashion. The column may rotate with respect to the cart, causing the tube arm to rotate with respect to the cart while fixed in relation to the column; additionally, the tube arm may radially extend and collapse, and translate linearly upwards and downwards along the column. The column may also contain multiple, nested segments which may extend to a point of maximal extension, and may collapse to a lowest, end position. In order to secure the tube arm for moving the mobile imaging system form one location to another, such as from one patient to another on a hospital floor, after operation of the mobile x-ray system, the tube arm may be placed in a parked position, and the column may be placed in a first collapsed position. Additionally, the column may further transition from the first collapsed position to an end position. Parking the tube arm and collapsing the column to an end position may make the mobile x-ray system more compact, and hence may allow for ease of transport for an operator of the mobile x-ray system.

In order to manipulate the imaging assembly and the tube arm, there may be a hand-actuatable component such as a first handle attached to the imaging assembly. Using the first handle, the operator may rotate the imaging assembly with respect to the tube arm and orient the tube arm in order to image a patient. In order to transport the mobile imaging system, the cart may have a second hand-actuatable component such as a second drive handle at the rear of the cart for the operator to push on. Using the second handle, the operator can drive the cart to a location, position the cart proximate to a patient's bed, and position the imaging assembly to image an anatomy of interest.

BRIEF DESCRIPTION

In one embodiment, a system comprises: upon conditions being met for moving a mobile imaging system, collapsing a column coupling an imaging assembly to a drive system while concomitantly moving the drive system. In this way, by concurrently driving the imaging assembly while collapsing the assembly to the end position, the time between consecutive scans using the mobile imaging system may be reduced.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 2:
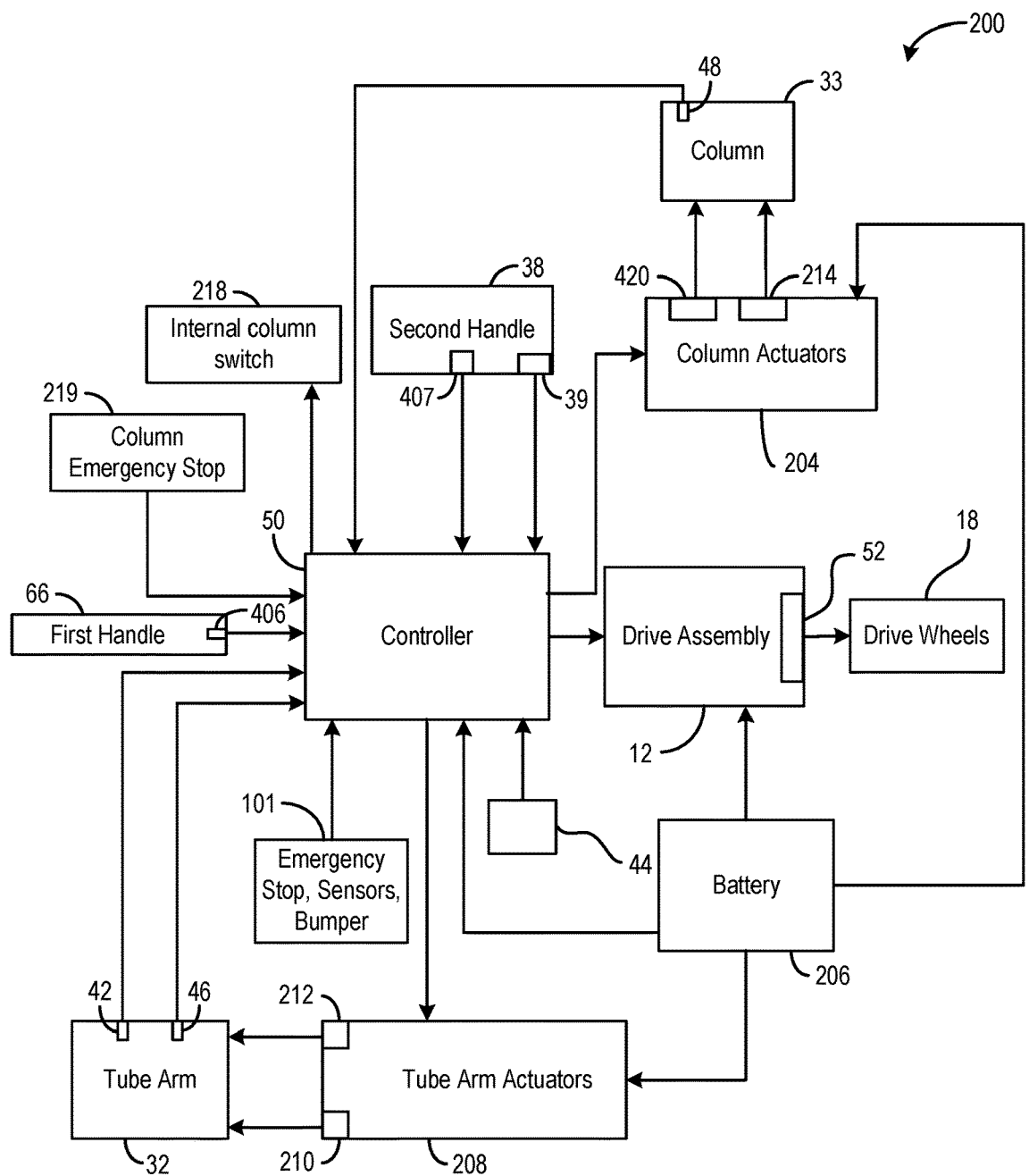
FIG. 2 shows a block diagram of actuation mechanisms for components of the mobile imaging system of FIG. 1.
Figure 3:
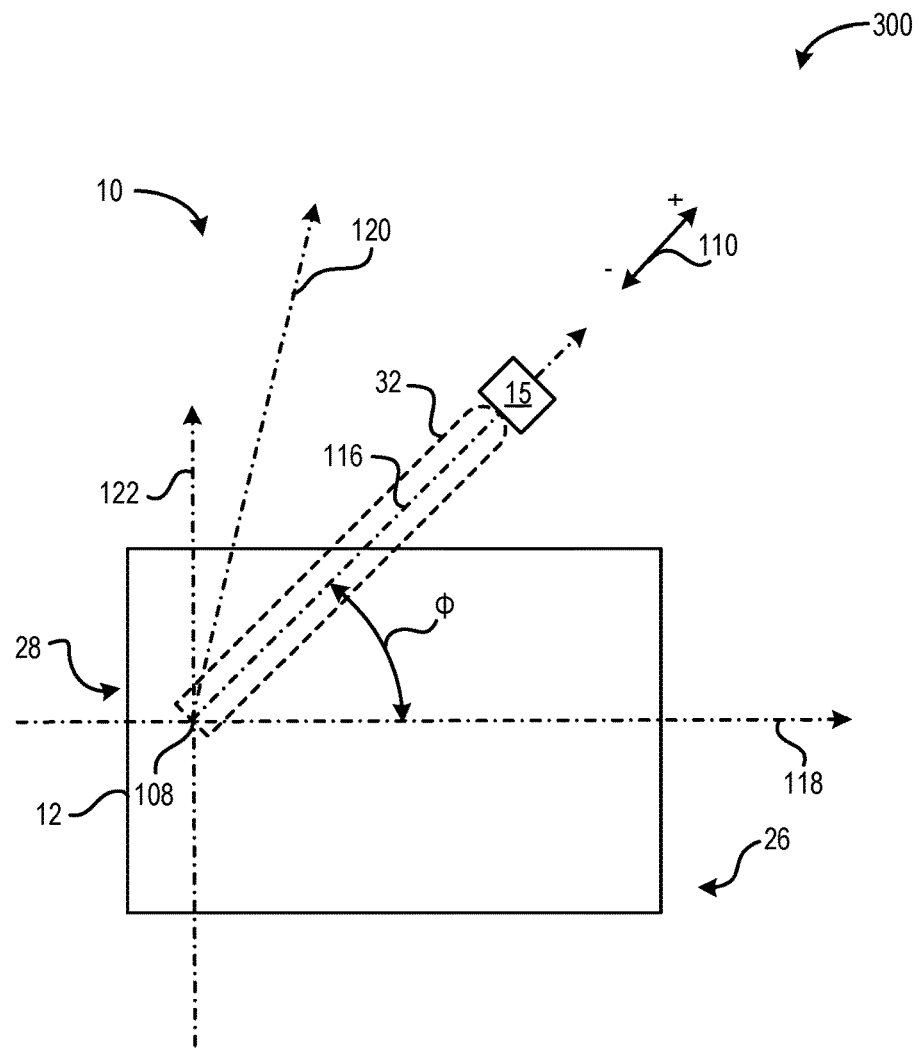
FIG. 3 shows a schematic diagram illustrating an orientation of assembly tube arm of the mobile imaging system of FIG. 1.
Figure 4A:
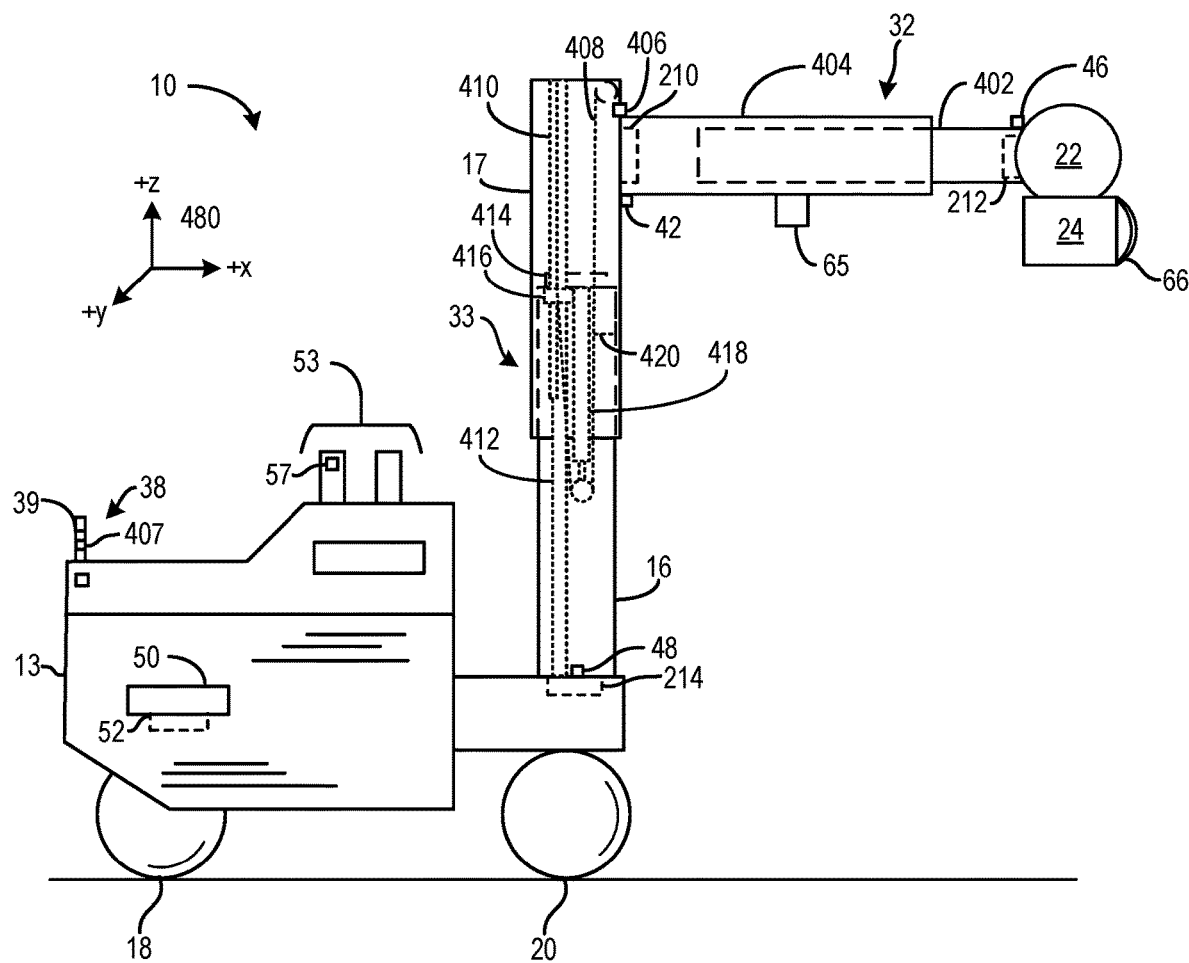
FIG. 4A shows an example embodiment of the mobile imaging system including a tube arm and a column in a first position.

The present disclosure relates to a mobile imaging system that allows a column of the mobile imaging system to be collapsed concurrently while allowing an operator to drive the mobile imaging system. An example embodiment of a mobile imaging system is given in FIG. 1, in particular showing a column containing two, nested segments. FIG. 2 shows a system architecture in a block diagram form for the mobile imaging system of FIG. 1. FIG. 3 shows an example orientation of the tube arm with respect to a cart of the mobile imaging system of FIG. 1. FIGS. 4A-E show example positions of the mobile imaging system in the process of transitioning from a first, operating position, to a fifth, fully collapsed position. In particular, FIGS. 4A-E illustrate the tube arm containing two, nested segments. FIGS. 5A-B show a flowchart illustrating an example method for transitioning the mobile imaging system from a first position as illustrated in FIG. 4A to a fifth position as illustrated in FIG. 4E.

As part of operating the mobile imaging system, in order to scan an anatomy of a patient, the operator may align the tube arm and a collimator mounted at the end of the tube arm at a particular orientation in relation to the patient. As an example, as part of aligning the mobile imaging system in relation to the patient, the mobile imaging system may be positioned proximate to the patient's bed. Further, the column may be in a fully extended position, the tube arm may be radially fully extended, and the tube arm (in conjunction with the column) may be rotated axially. After the operator has finished the imaging process, it may be desired to shift the system to a different location. The mobile imaging system may be reoriented from the operating position to a fully collapsed position, which may be efficient for transportation of the cart. The fully collapsed position may include the tube arm being fully radially retracted, being fixed to a cart of the mobile imaging system via a latch in a parked position, and the column being collapsed to a lowest, end position.

As part of the transition of the mobile imaging system from an imaging orientation to a fully collapsed position for transport, the operator may have to wait for the tube arm to first return to a fully parked position before the column begins to fully collapse. After the tube arm is parked and the column is fully collapsed in an end position, the operator may begin to drive the cart. This process may be time consuming in an environment where the operator may have many patients to attend within strict time constraints (e.g. in an intensive care unit or emergency room environment).

In one example, parking of the tube arm may be initiated by exerting force on a first handle coupled to the imaging assembly. An imaging assembly may be coupled to the column via a rotatable and extendable tube arm, with a column coupling the tube arm to a drive system. Tube arm parking may be carried out by rotation of the tube arm to an origin position, retraction of the tube arm towards the column to a fully retracted position, and driving the tube arm vertically downwards along the column. Further, the retraction of the tube arm may be based on a first input from a first position sensor coupled to the column indicating a radial position of the tube arm, the driving of the tube arm vertically may be based on a second input from a second position sensor coupled to the tube arm indicating a vertical position of the tube arm relative to the column, and the rotation of the tube arm may be based on a third input from a third position sensor coupled to the column indicating an angular displacement of the column and the tube arm relative to the origin position. Each of the column and the tube arm may be moved linearly downwards even after the operator releases the first handle. While the tube arm is transitioned to a parked position and the column is transitioned to a first collapsed position, the operator may initiate movement of the cart by application of force to a second handle. After the tube arm and column are in a parked position, the operator may then initiate collapsing of the column to an end position via either a drive handle switch or by continuing to exert force on the second handle while driving the cart. As an example, the motion of the column from a parked position to a fully collapsed position may be carried out concomitantly while driving the cart forward. While the column may collapse at a constant speed, the speed of movement of the cart may be adjusted based on force feedback from the second handle.

In this way, by not waiting for the column to fully collapse before starting to drive the cart, the mobile imaging system may be transported faster to a desired location, thereby saving valuable time in a hospital floor. Tube arm parking actuation in response to an initial operator input to a first handle even after release allows the system to more efficiently transition to a position where the tube arm is secured for travel. In addition, the operator may initiate movement during tube arm parking, allowing a quicker transition from imaging to transport. Collapsing the column while concurrently driving the cart may provide a timesaving mechanism while still minimizing any visual impediment caused by the column. Overall, by expediting parking of the tube arm and collapsing of the column to the end position without waiting to drive the cart, workflow of the user may be made more efficient.

Figure 1:
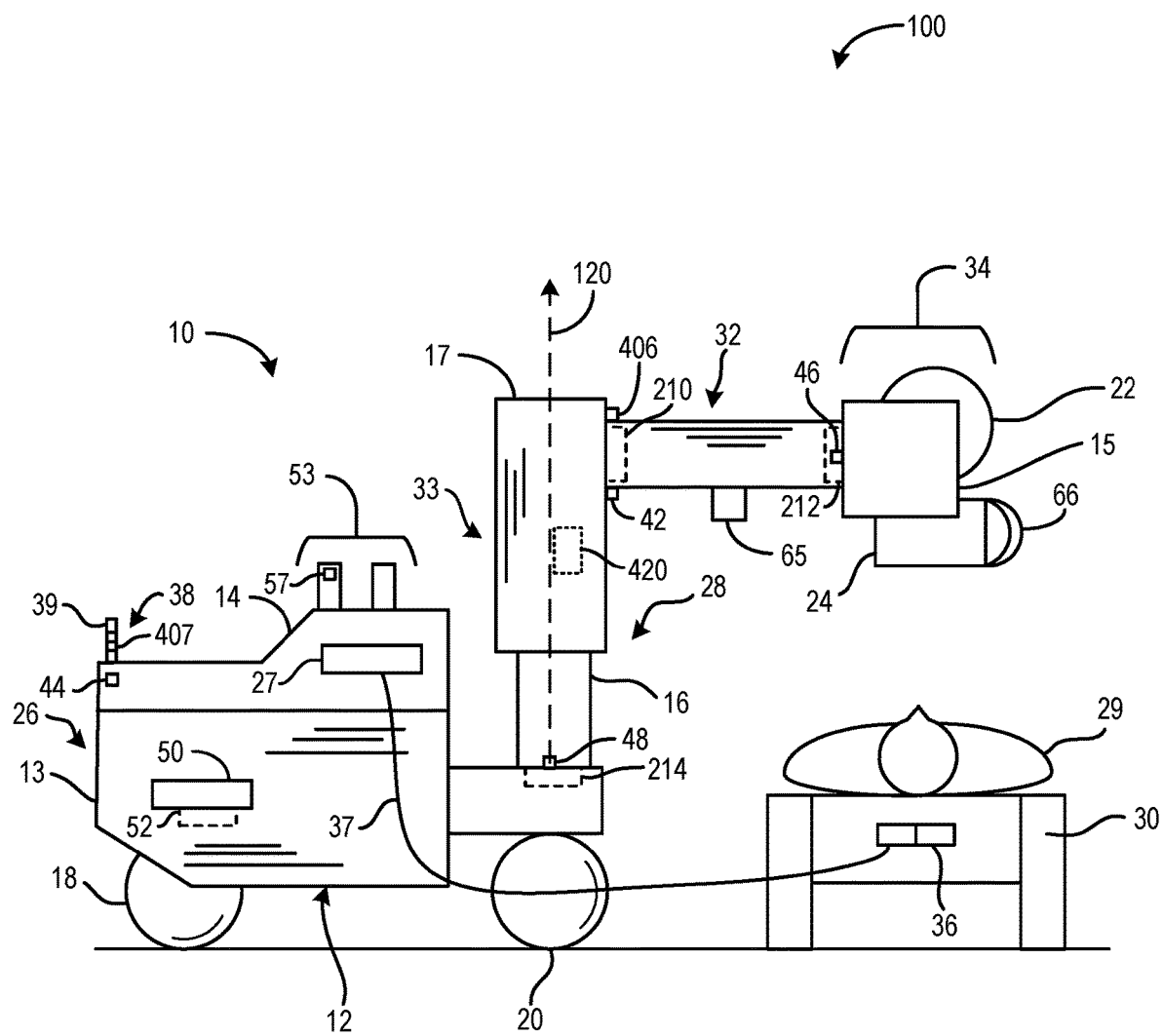
FIG. 1 shows an elevation view of an example mobile imaging system.

FIG. 1 illustrates an example 100 of a mobile imaging system 10 that may be used in the medical field or in other fields. The mobile imaging system 10 has a drive assembly 12 and an operator console 14 that may be supported by the drive assembly 12. The drive assembly 12 comprises a frame 13 (also referred to herein as a cart) and two rear drive wheels 18 (one wheel is shown) coupled to the frame at a rear end 26 of the mobile imaging system 10 and two front wheels 20 (one wheel is shown) coupled to the frame at a front end 28 of the mobile imaging system 10.

A column 33 is attached to, and extends upwardly from, the frame of drive assembly 12 and rotates or swivels with respect to the drive assembly 12. Column 33 contains an outer segment 17, and an inner segment 16, which is nested within the outer segment 17. The inner segment 16 is fixed to the cart 13, while the outer segment 17 may telescope outwards from the inner segment 16 in response to operator manipulation. The outer segment may have a range of motions defined by a maximum focal point (where the column 33 is fully extended and the segments 16 and 17 have a minimal overlap) and a minimum focal point (where column is fully collapsed in an end position, with the outer segment fully encapsulating the inner segment). A tube arm 32 is fixed to the column 33, extending perpendicular to the column. The tube arm 32 may be vertically adjustable relative to the column 33, and may be otherwise fixed in its position relative to the column. In other words, the tube arm 32 may not rotate independently of the column 33, but may co-rotate with the column as the column rotates with respect to the cart 13. The tube arm may translate vertically along and independently along the axis 120 defined by the length of the column 33, e.g., in response to user manipulation. The tube arm 32 may also telescope (such as project in and out horizontally) with respect to the column 33, allowing components mounted at an outer end of the tube arm 32 to be moved closer to or further away from the column 33.

An imaging assembly, herein in the form of a radiation source 34 including an x-ray source assembly 15, is attached to the outer end of the tube arm 32 and has an x-ray tube housing 22 containing an x-ray source (not shown). A collimator 24 is attached to the tube housing 22 and is rotatable with respect to the tube housing 22. An x-ray detector 36 detects x-ray data and may communicate with an imaging controller 27 wirelessly or over a cable 37. Attached to the imaging assembly is a first hand-actuatable handle 66 (herein referred to as a first handle), which an operator may use to orient the tube arm and imaging assembly relative to the cart.

The tube arm 32 may include a first force sensor 406. As an example, the first force sensor 406 may be placed on the top side of tube arm 32, at the base of the tube arm 32 where the tube arm meets the column 33. First force sensor 406 may measure forces along three independent, mutually perpendicular axes, such as a radial force applied to the first handle 66, which may act to either expand or retract the tube arm 32, a vertical force applied to the tube arm 32, which may act to translate linearly upward or downward the tube arm 32 in relation to the column 33, and a tangential force applied to the first handle 66, which may act to co-rotate the column 33 and tube arm 32. Additionally, first force sensor 406 may be coupled to a wire rope contained within column 33. The wire rope may exit the outer segment 17 of the column and attach to the tube arm proximate to the first force sensor 406, and the first force sensor 406 may be further configured to measure the force on the tube arm 32 due to the wire rope (as described in relation to FIGS. 4A-E). Signals generated by first force sensor 406 in response to the forces applied to the first handle 66 may be sent to a controller 50, which may then actuate motion of the tube arm 32 and/or the column 33, as described in more detail in FIG. 2.

Sensors may be included in the imaging assembly to measure either position and/or acceleration of various components. As an example, a first position sensor 42 coupled to the tube arm 32 may estimate the position of the tube arm 32 relative to the column 33 and the cart 13, which may be used to estimate the extent of radial extension or retraction of the tube arm 32. During actuation of the tube arm 32, the first position sensor 42 may send a signal to controller 50, which may then actuate further radial motion of the tube arm 32, as described in more detail in relation to FIG. 2. In another example, a second position sensor 46 may be coupled to the tube arm 32 to estimate the vertical position of the tube arm 32 (along the axis 120) relative to the column 33. The second position sensor 46 may send a signal to controller 50, which may then actuate vertical translation of the tube arm 32 with respect to the column 33, as described in more detail in relation to FIG. 2. Sensors 42 and/or 46 may be optical sensors, magnetic sensors, pressure/force sensors, inertial measurement units (IMUs), or any variation of these sensors. It may be noted that the sensors of the various embodiments may be any suitable type or types of sensors. For example, one or more of the sensors may operate based on sensing a change in distance using optical, magnetic, electrical, or other mechanisms. In an additional example, a third position sensor 48 may be coupled to the column 33, to estimate the angular displacement of the column 33 relative to the cart. The third position sensor 48 may send a signal to controller 50, which may then adjust rotational motion of the column 33, as described in further detail in relation to FIG. 2. The sensor 48 may be an optical sensor, magnetic sensor, Hall effect sensor, or other suitable sensor adapted to detect the degree of rotation of column 33. The placement of sensors 42, 46, and 48 as shown in FIG. 1 is exemplary, and other configurations are possible.

A second hand-actuatable interface is provided on system 10, in the form of a second drive handle 38 (herein referred to as the second handle 38) provided on the rear end 26 of the system 10, such as coupled to the frame of drive assembly 12. Controller 50 senses or receives signals based on the manipulation (e.g., user manipulation) of the second drive handle 38, and the mobile imaging system 10 may be driven to different locations to image patients. As an example, the second handle 38 may detect a force applied to the handle via a second force sensor 407 contained within the handle, which may then send a signal to controller 50 to actuate the drive assembly 12. The drive assembly 12 may include a drive motor 52, and is capable of driving the rear drive wheels 18.

A patient or subject 29 is typically positioned on a bed or table 30. Once the mobile imaging system 10 is stationed near the table 30, the column 33 is swiveled or rotated (e.g., via user manipulation) to position the x-ray source assembly 15 directly over the anatomy of the subject 29 to be scanned. The detector 36 is positioned on the opposite side of the subject 29.

A user interface 44 may be provided proximate the rear end 26 of the system 10. Optionally, the user interface 44 may be integrated with the second handle 38 or it may be configured as a remote control that may be held in the operator's hand away from the system 10. The user interface 44 may communicate with the controller 50 wirelessly or over a wired connection. The user interface 44 may be one of, or a combination of, a button, joystick, toggle switch, power assist handle, provided as a key on a keyboard or a selection on a touchscreen, and the like. In some examples, the signals sent by the second handle 38 may be different than the signals sent by the user interface 44. For example, the user interface 44 may send signals to switch drive modes, power on or off the system 10, etc.

The controller 50 receives information from a plurality of sensors that indicates the position of the column 33, tube arm 32, collimator 24, and/or x-ray source assembly 15. Further, controller 50 may receive force information that indicates the extent of force applied to the first handle 66 and the second handle 38. In response to positional and force information, controller 50 may actuate a plurality of motors (such as a first servomotor 210, a second servomotor 212, a third servomotor 214, the drive motor 52, and a column motor 420, all of which will be discussed further in relation to FIG. 2), which may control the motion of the tube arm 32, the column 33, and the drive wheels 18 of system 10. Additionally, controller 50 may receive signals from user interface 44, as described above.

FIG. 2 illustrates an example 200 of control system and components for actuation of each of the column, the tube arm, and the drive assembly of the mobile imaging system 10 of FIG. 1.

The mobile imaging system 10 may be controlled via a controller 50, which may receive signals from a plurality of sensors further described herein.

In order to actuate motion of the tube arm 32, the controller 50 may receive signals from a first handle 66 via a first force sensor 406. The first handle 66 may be coupled to the first force sensor 406, as described in relation to FIG. 1. The output of the first force sensor 406 may estimate a force applied on the first handle. Upon receiving force signals from first force sensor 406, controller 50 may initiate motion of the tube arm via tube arm actuators 208. Tube arm actuation may include two independent degrees of motion of the tube arm 32: radial expansion and retraction of the tube arm 32 and vertical translation of the tube along the column. For each of the independent degrees of motion of the tube arm 32, there is a corresponding servomotor, the first servomotor 210 and the second servomotor 212, to provide force feedback along the respective degrees of motion (as described further in relation to FIG. 2). Additionally, there may be the third servomotor 214 to provide force feedback for rotation of the column with respect to the cart, in response to a signal received from the first handle 66.

A servomotor may contain a motor coupled to a position sensor, which may then send a signal to the motor for actuation in response to the position information. As an example, a servomotor may contain an internal position encoder, such as a rotary encoder, which may estimate the angular position of a shaft contained within the motor. The positional information of the shaft contained within the motor may then be sent to a controller to actuate the motor. Additionally or alternatively, a servomotor may contain an external position sensor, which may record the position of a component external to and driven by the motor. The signal obtained from the external position sensor may then be sent to a controller to actuate the motor. Further, a servomotor can be configured to actuate in response to signals from a force sensor, in conjunction with positional signals received from a position sensor.

As an example, the first servomotor 210 may provide power for radial expansion and retraction of the tube arm. This may involve receiving the force information from first force sensor 406 of force applied radially along the tube arm, in addition to positional information from first position sensor 42 of an outer segment of the tube arm 32 (as described in relation to FIGS. 4A-E). The force and positional information obtained from sensors 406 and 42 respectively may then be sent to controller 50 to actuate the second servomotor 212 to apply power to radially expand or contract tube arm 32 at a set velocity. The set velocity of the tube arm 32 may be determined via a force feedback loop based on the radial force estimated from the first force sensor 406.

As an example of the above force feedback loop, a first proportional integral (PI) controller may be used to adjust power delivered to the first servomotor 210. A setpoint of the first PI controller may be adjusted based on each of the output of the first force sensor 406 and the output of the first position sensor 42. The first PI controller may receive a difference between a setpoint power and actual power delivered to the first servomotor 210. At the first PI controller, the error may be processed and/or modified (scaled) by a proportional gain. The integral of the error may be similarly processed and/or modified (scaled) by an integral gain. One of these terms or their sum is then output as a signal. The output signal of the first PI controller may produce the final control signal to be sent to the motor of the first servomotor 210.

As another example, the second servomotor 212 may provide power for vertical translation of the tube arm 32 along the column 33. The second servomotor 212 may first receive force information from first force sensor 406 of force applied vertically along the tube arm, in conjunction with positional information from sensor 46 of the tube arm 32 along the height of the column. The force and positional information obtained from sensors 406 and 46 respectively may then be sent to controller 50 to actuate the second servomotor 212 to apply power to translate tube arm 32 upwards or downwards at a set velocity. The set velocity of the tube arm 32 may be determined via a force feedback loop based on the vertical force estimated from first force sensor 406.

As an example of the above force feedback loop, a second proportional integral (PI) controller may be used to adjust a power delivered to the second servomotor 212. A setpoint of the second PI controller may be adjusted based on each of the output of the first force sensor 406 and the output of the second position sensor 46. The second PI controller may receive a difference between in a setpoint power and actual power delivered to the second servomotor 212. At the second PI controller, the error may be processed and/or modified (scaled) by a proportional gain. The integral of the error may be similarly processed and/or modified (scaled) by an integral gain. One of these terms or their sum is then output to a signal. The output signal of the second PI controller may produce the final control signal to be sent to the motor of the second servomotor 212.

Similarly, the third servomotor 214 may provide power for axial rotation of the column 33. This may involve receiving the force information from first force sensor 406 of a tangential force on the tube arm, in addition to angular positional information from third position sensor 48. The force and positional information obtained from sensors 406 and 48 respectively may then be sent to controller 50 to actuate the third servomotor 214 to apply power to rotate column 33 at a set velocity. The set velocity may be determined via a force feedback loop based on the tangential force estimated from first force sensor 406.

As an example of the above feedback loop, a third proportional integral (PI) controller may be used to adjust a power delivered to the third servomotor 214. A setpoint of the third PI controller may be adjusted based on each of the output of the first force sensor 406 and the output of the third position sensor 48. The third PI controller may receive a difference between in a setpoint power and actual power delivered to the third servomotor 214. At the third PI controller, the error may be processed and/or modified (scaled) by a proportional gain. The integral of the error may be similarly processed and/or modified (scaled) by an integral gain. One of these terms or their sum is then output to a signal. The output signal of the third PI controller may produce the final control signal to be sent to the motor of the third servomotor 214.

Additionally, each of the servomotors 210, 212 and 214 respectively may include internal velocity sensors. In alternate embodiments, the position sensors (such as first position sensor 42, second position sensor 46, and third position sensor 48) may be replaced with accelerometers.

Controller 50 may also receive input signals from several other sources, including the user interface 44, an emergency stop mechanism 101, an emergency column drive stop mechanism 219, and a column switch 218. At any time during operation, controller 50 may be configured to receive and act upon an input from one or more emergency stop mechanisms 101, which may include one or more of a button, sensor, bumper and the like, and which may act to deactivate the drive wheels 18. Controller 50 may also be configured to receive and act upon inputs from a column drive stop mechanism 219. As an example, the column stop mechanism 219 may deactivate further collapse of the column in response to e.g. insufficient power from a battery 206. As a further example, controller 50 may discontinue actuation of the column motor 420 in response to the column switch 218. As another example, if the column is in a fully collapsed, end state, the column switch 218 may indicate that the column is in a fully collapsed position, which may cause the controller 50 to deactivate further collapse of the column 33.

Additionally, example control system 200 may include the drive assembly 12, which houses drive motor 52. The drive motor 52 may actuate the drive wheels 18 via controller 50 in response to a force signal detected by the second force sensor 407 contained within the second handle 38. The drive wheels 18 may rotate at a speed may be determined by the force detected by the second force sensor 407 via a force feedback mechanism. Said another way, moving the drive system may include actuating a set of drive wheels 18 coupled to the drive system with a speed of the drive wheels 18 adjusted based on signals received from a second force sensor 407 coupled to the second handle 38. The force feedback mechanism for drive motor 52 may be substantially similar to the force feedback mechanisms for servomotors 210, 212, and 214, whereby the drive motor 52 may provide power to the drive wheels 18 in response to the force applied to the second handle 38. The power applied to the drive wheels 18 by drive motor 52 may then cause the drive wheels 18 to rotate at a set speed, the set speed determined by the force applied to the second handle 38.

The second handle 38 may also contain a drive switch 39, which may actuate the column collapsing from a first, collapsed state to a fully collapsed state (as described in relation to FIGS. 4D-5B).

Further, example control system 200 may include column actuators 204, which may contain the aforementioned third servomotor 214, and the column motor 420. Column motor 420 may be a servomotor, which may contain a motor and an internal position sensor (such as an encoder or potentiometer), the latter of which may record positional information about the shaft within the column motor 420. The degree of extension of the column 33 may be inferred from positional information of the internal position sensor of column motor 420, with end of travel positions defined by predefined values within the extension range. Additionally, column motor may receive force information from the first force sensor 406, and may provide power for the collapse of the column 33 based off of force information from the first force sensor 406, and positional information of the degree of extension inferred from the internal position sensor of column motor 420. Additionally or alternatively, the column motor 420 may provide power for collapsing the column based off of input from the drive switch 39. As a first example, in response to force applied to the second handle 38, column motor 420 may drive down the column 33 at a set velocity, the velocity determined by the force applied to the second handle 38 via a force feedback mechanism. As a second example, the column motor may drive down the column 33 at a fixed velocity in response to input from the drive switch 39.

The actuators of system 10, such as the column actuators 204, the drive assembly 12, and the tube arm actuators 208, in addition to the controller 50, may be powered by battery 206, which may be a rechargeable energy storage device.

FIG. 3 is a schematic diagram 300 illustrating the orientation of the drive assembly 12 and tube arm 32 with respect to each other. The column 33 (not shown in FIG. 3) pivots with respect to the drive assembly 12 at a pivot point 108. For example, referring to FIG. 1, a center of the column 33 may define the pivot point 108. The drive assembly 12 may have a coordinate system, containing of a longitudinal axis 118, which extends parallel to the length of the drive assembly 12 and is centered symmetrically along the length of the drive assembly 12, a latitudinal axis 122, which extends perpendicular to the longitudinal axis 118 and intersect the longitudinal axis 118 at the pivot point 108, and a vertical axis 120, defined by the length of the column (not shown). The vertical axis 120 is perpendicular to both the longitudinal axis 118 and the latitudinal axis 122, and intersects both at the pivot point 108.

As shown in FIG. 3, the column 33 is pivoted with respect to the longitudinal axis 118 such that a center line 116 of the tube arm 32 is at an angle of rotation Φ with respect to the longitudinal axis 118. As used herein, the angle of rotation Φ is equal to zero when the center line 116 of the tube arm is coincident with the longitudinal axis 118, and may describe the angle of rotation Φ of the column 33 with respect to the longitudinal axis 118. As the tube arm 32 co-rotates as the column 33 rotates and may not rotate independently of the column 33, the angle of rotation Φ may also refer to the angle of rotation of the tube arm 32 with respect to the longitudinal axis. The angle of rotation Φ may increase (with positive values) as the column is rotated clockwise and increase with negative values as the column is rotated counter clockwise. The angle of rotation Φ when the tube arm 32 is in the parked position is 0, so that the tube arm 32 is parallel with the longitudinal axis 118. Additionally, the tube arm 32 may expand and retract along the axis defined by the center line, as indicated by 110.

FIGS. 4A-E show various configurations of the mobile imaging system 10 in transition from a first position in an imaging orientation to a final position during transportation of the imaging system. Additionally illustrated in FIGS. 4A-E are arrows indicating motion of various parts of mobile imaging system 10 during transitions between positions, and a coordinate system 480 indicating mutually perpendicular directions x, y and z.

FIG. 4A shows mobile imaging system 10 in a first position. A first position may be a position in which the mobile imaging system 10 may be in an imaging configuration for imaging a patient (not shown). As an example, the first position may include the column 33 being fully extended to a maximal length, the tube arm 32 being extended radially to a maximal length, and the angle of rotation Φ of the column 33 and tube arm 32 with respect to the longitudinal axis is 180 degrees. As examples, the extent of extension of the column 33, extent of extension of the tube arm 32, and the non-zero angle of rotation Φ of the column 33 and the tube arm 32 for the imaging configuration may take on a range of values.

The internal components of tube arm 32 and column 33 are shown in FIG. 4A. The tube arm 32 is shown to contain an inner segment 402, which is nested within an outer segment 404, and may extend and contract within a predefined range of motion along an axis of the tube arm (such as the axis defined by the center line 116 of the tube arm 32, as shown in FIG. 3). Also shown within the tube arm 32 are the tube arm actuators 208, which may include servomotors 210 and 212 for two independent degrees of motion of the tube arm, as described in detail for FIG. 2. However, the exact placement of tube arm actuators 208 and the servomotors contained therein is exemplary. Contained within the column 33 are a variety of components which may actuate the collapse of the column 33 to an end position. Housed within both the inner segment 16 of the column 33 and the outer segment 17 of the column 33 is a first gas spring 412, which may provide a counterbalancing force to the tube arm and column, additional external loads of the cart 13, and friction between the inner segment 16 and the outer segment 17, aiding in positioning the column 33 at a particular height. The first gas spring 412 is extendable along the full length of the inside of the column 33. Proximate to first gas spring 412 is ball screw 410, which is housed within both the inner segment 16 and the outer segment 17, and is fixed to the top of the inside of outer segment 17. Ball screw 410 may be actuated by a ball nut 416, which is housed within inner segment 16, and may be driven by a column motor 420 via a belt drive 414. The column motor is housed within inner segment 16, while the belt drive is placed externally on the top of inner segment 16. The ball nut 416 may rotate in response to actuation by column motor 420 via belt drive 414, and may lower the outer segment 17 by the induced downward motion of ball screw 410 due to rotation of ball nut 416.

Also internal to the column 33 is a tension gas spring 418 (herein referred to as the second gas spring), which is housed within the inner segment 16 and fixed internally to the top of inner segment 16. Second gas spring 418 may expand and contract within the inner segment 16, and may transmit an upward force to the tube arm 32 via a wire rope 408. The wire rope 408 is attached to the top of the inside of the inner segment 16, and is under tension and in contact with the second gas spring 418 via a pulley attached to the second gas spring. The wire rope 408 exits from the top of the inner segment 16 and wraps around another pulley within the interior of the outer segment 17, exiting the outer segment and attaching outside of the tube arm 32. The wire rope 408 is of a fixed length, and may be put under increasing tension due to increased expansion of the of second gas spring 418. In the first position of FIG. 4A, the second gas spring 418 is compressed, and the wire rope 408 extends within the interior of the extended outer segment 17.

Figure 4B:
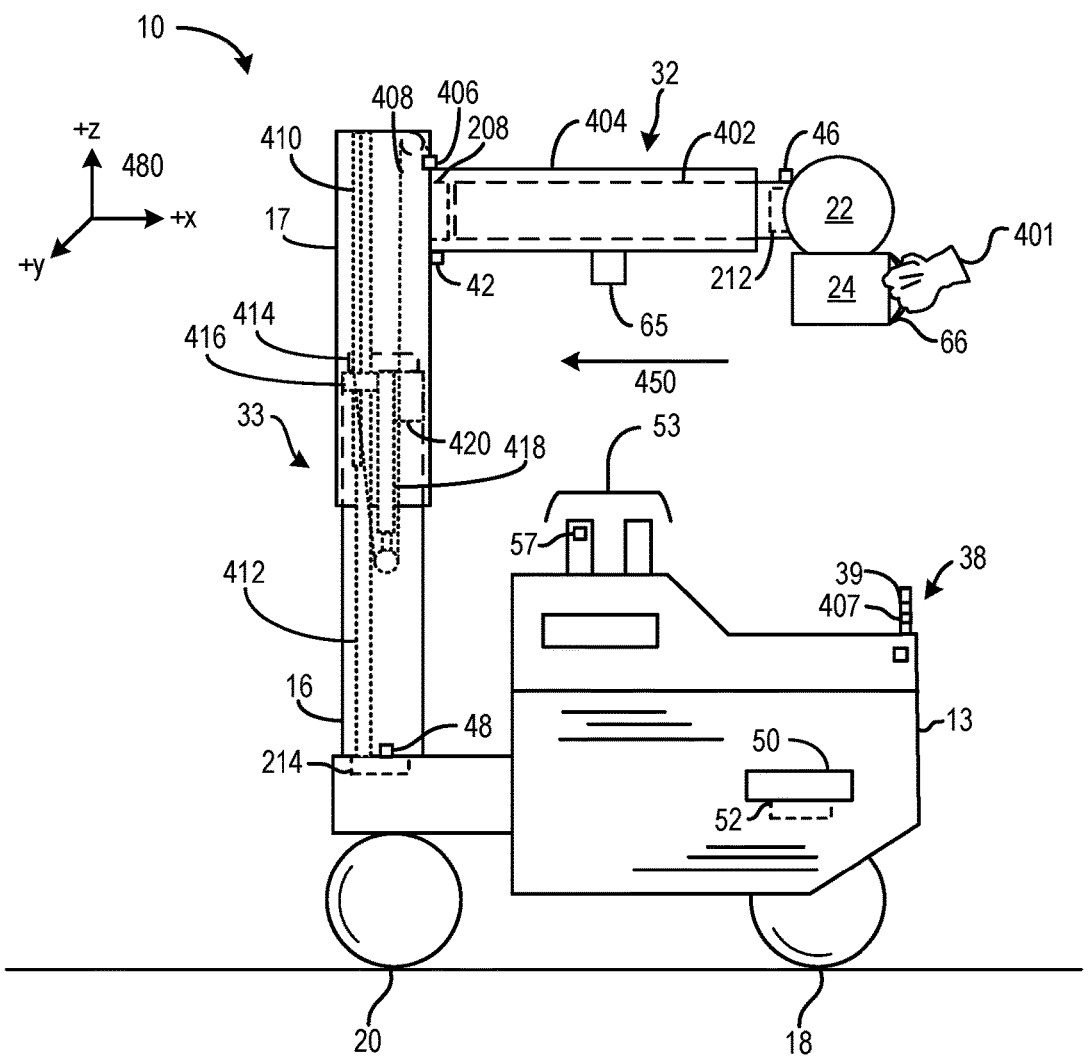
FIG. 4B shows an example embodiment of the mobile imaging system in a second position.
Figure 5A:
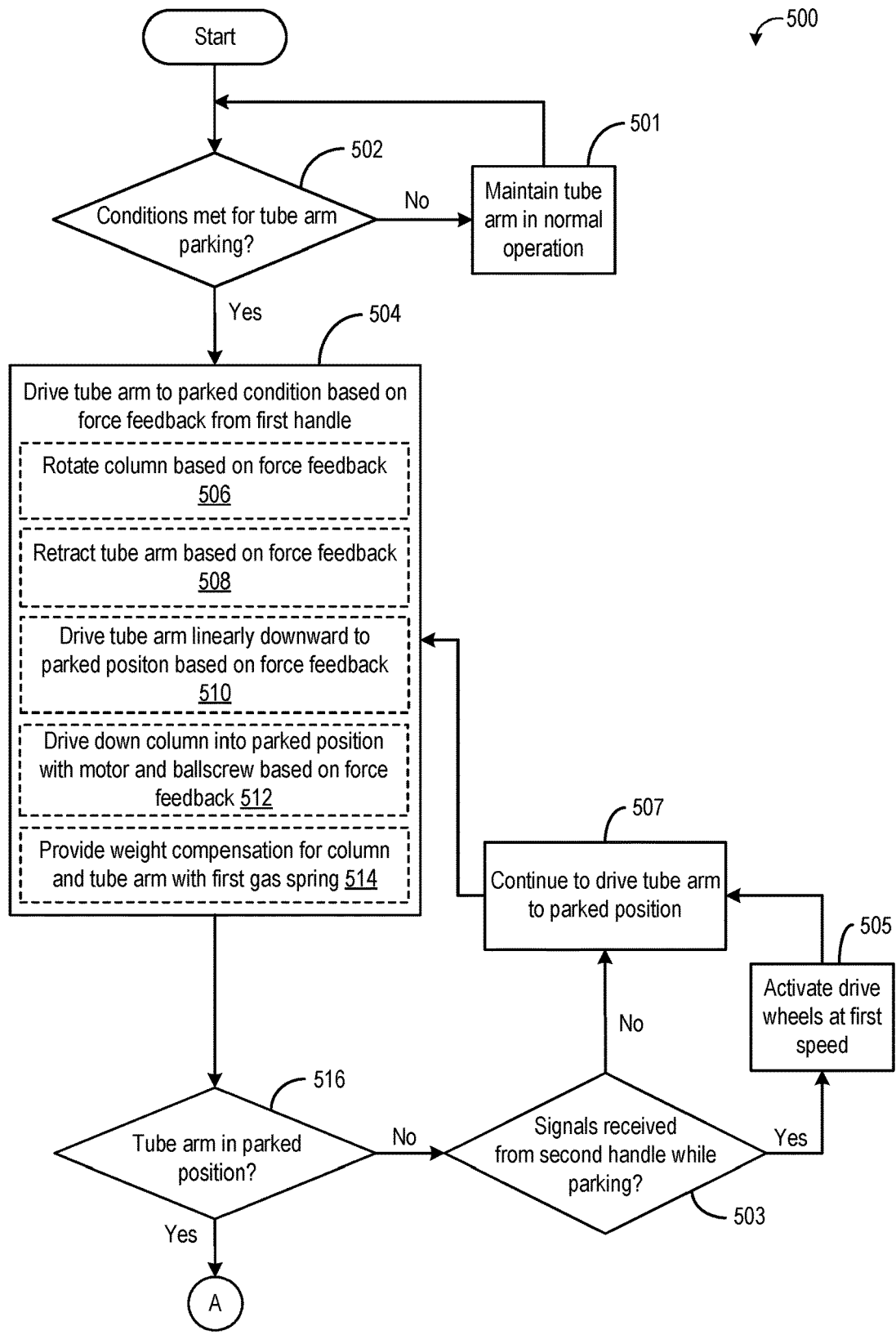
FIG. 5A-5B show a flowchart illustrating an example method for collapsing the column while driving the mobile imaging system.
Figure 5B:
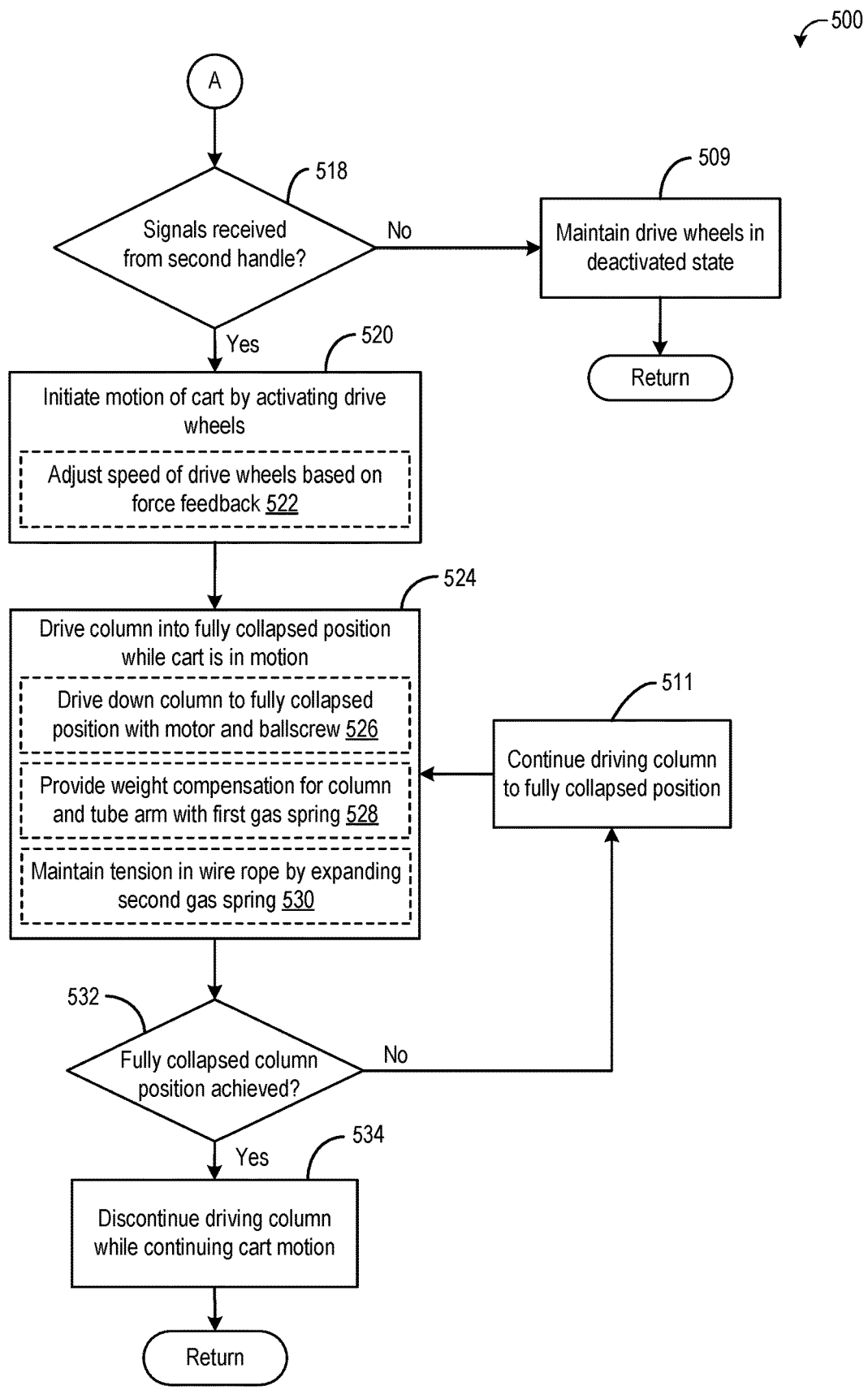

FIG. 4B shows mobile imaging system 10 transitioning from a first position to a second position. The second position may contain the tube arm 32 rotated from an imaging orientation (an example angle of rotation Φ of the column 33 and the tube arm 32 is given as 180 degrees in FIG. 4A) to an origin position, where the angle of rotation Φ of the column 33 and the tube arm 32 is 0 degrees. The second position may also include the tube arm 32 to be in a fully retracted position. The tube arm rotation may be due to the force applied to the first handle 66 by an operator 401. In response to force applied to the first handle 66 by an operator 401, a third servomotor (such as third servomotor 214 of FIGS. 1-2) may act to drive tube arm rotation at a set velocity determined by the applied force via a force feedback mechanism. Additionally, FIG. 4B illustrates tube arm retraction from a fully extended position (as shown in FIG. 4A) to a fully retracted position. The tube arm retraction may be due to force applied to the first handle 66 by operator 401, and in response to force applied to the first handle 66 by an operator 401, a first servomotor (such as first servomotor 210 of FIGS. 1-2) may act to drive tube arm retraction at a set velocity determined by the applied force via a force feedback mechanism. The retraction motion of the tube arm 32 is indicated by arrow 450 parallel to the x axis of coordinate system 480.

Figure 4C:
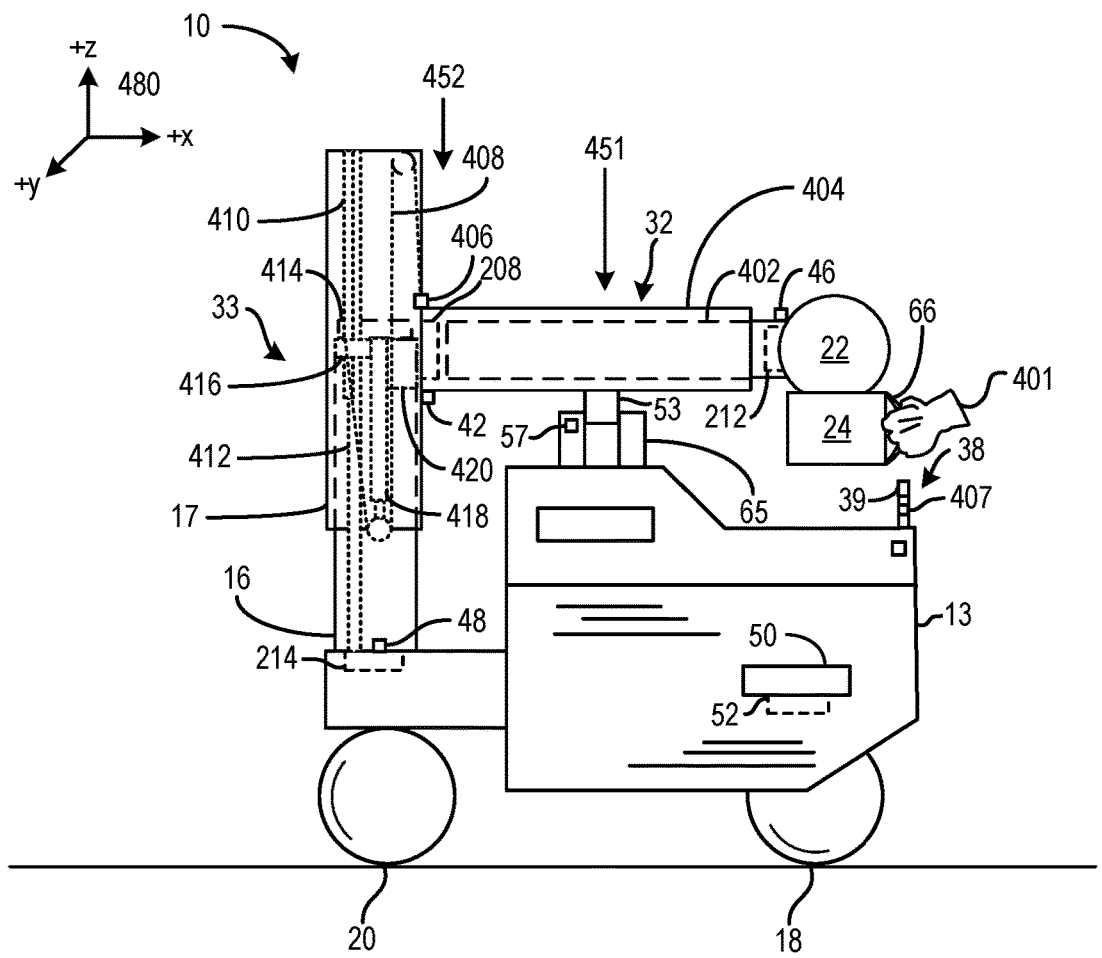
FIG. 4C shows an example embodiment of the mobile imaging system in a third position.

FIG. 4C shows mobile imaging system 10 transitioned from a second position to a third position. The third position may include the tube arm 32 fully retracted and in a parked position. The parked position may include the tube arm 32 being fully radially retracted, the tube arm being aligned parallel to the longitudinal axis 118 with angle of rotation Φ of the tube arm 32 being 0, and the tube arm 32 being in a vertically lowered position relative to the column 33, being fastened to the cart 13 via latches 53 and 65. Additionally, as part of the parked position, column 33 may be in a first collapsed position. The tube arm may be translated vertically from a maximum focal point (as shown in FIG. 4B) to a parked position due to the force applied to the first handle 66 by the operator 401; this motion is indicated by arrow 451 parallel to the z axis of coordinate system 480. The vertical translation of the tube arm 32 may be based on force feedback in response to a force applied to the first handle 66 by operator 401 via a second servomotor (such as the second servomotor 212 of FIG. 2). The velocity of the tube arm parking may be set, via force feedback, based on the force applied by the operator 401 to the handle 66. Additionally, after an initial downward force applied to the first handle 66 by operator 401, the operator 401 may let go of the first handle 66, and the tube arm may continue to translate vertically along the axis 120 at a fixed velocity, determined by the velocity of the tube arm upon release of the handle, and the force applied to the handle upon release. As the tube arm 32 is lowered to the parked position, tube arm 32 may attach to cart 13 via latches 53 and 65, which are attached to the tube arm 32 and the cart 13, respectively. The latches 53 and 65 may indicate to the controller 50 that the tube arm is in a parked position upon fastening via latch sensor 57. Concomitantly with the tube arm parking, the outer segment 17 of the column 33 may partially retract from a maximal focal point to a first collapsed position in response to the force applied to the first handle 66 by operator 401. The force applied to first handle 66 is estimated by first force sensor 406, which detects the direction and magnitude of the force, and actuates the column motor 420 to retract the column via controller 50. The retraction motion of the outer segment 17 is indicated by arrow 452 parallel to the z axis of coordinate system 480. The column motor 420 drives the ball nut 416 via belt drive 414, which induces a downward motion of ball screw 410, lowering the outer segment 17. As an example, the column first collapsed position may be 50% between the fully extended and fully collapsed positions.

Figure 4D:
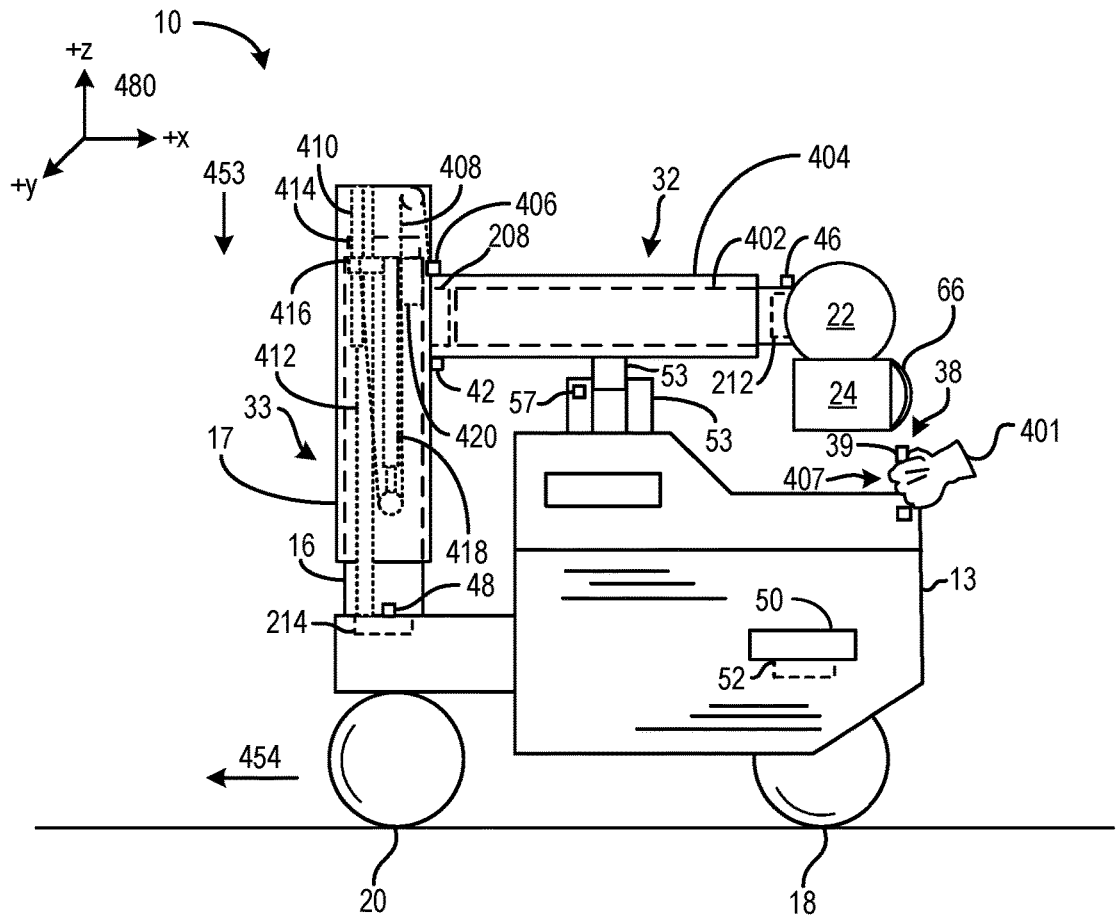
FIG. 4D shows an example embodiment of the mobile imaging system in a fourth position.
Figure 4E:
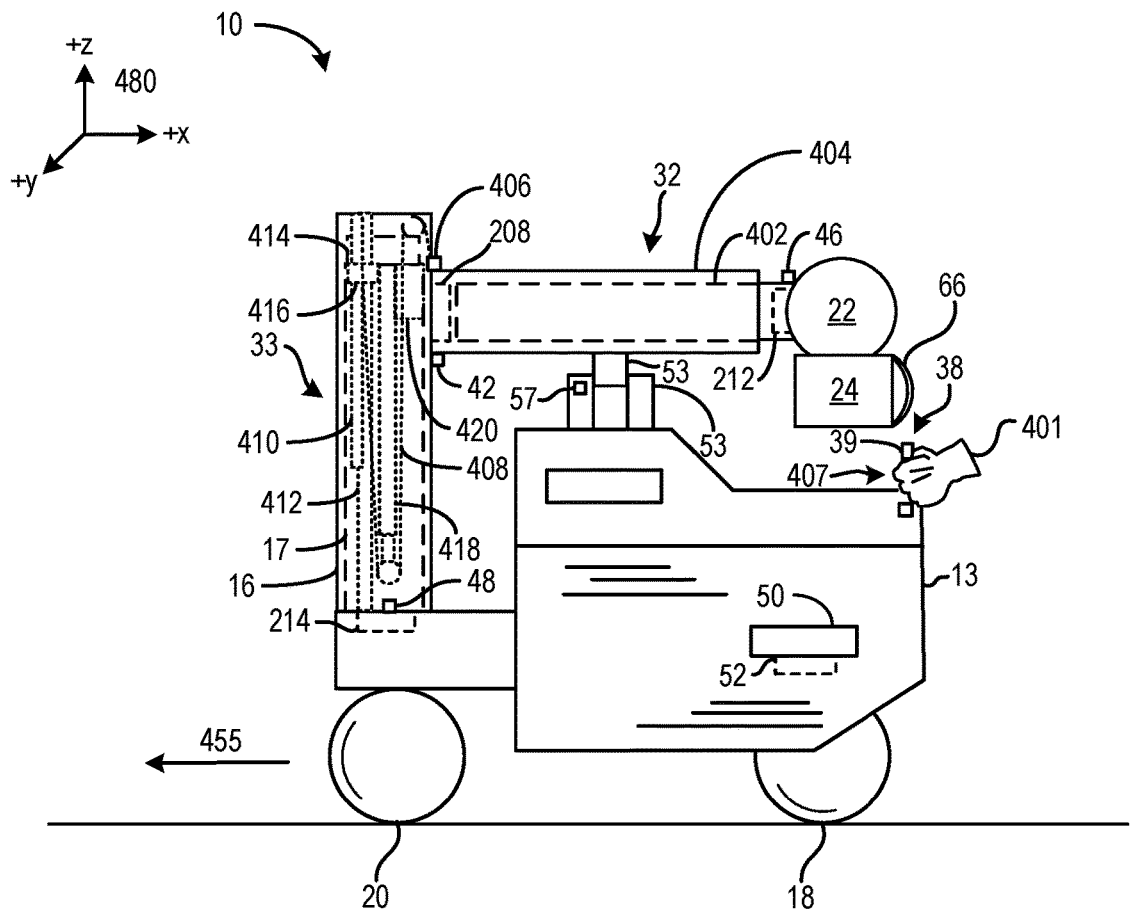
FIG. 4E shows an example embodiment of the mobile imaging system in a fifth position.

FIG. 4D shows mobile imaging system 10 transitioned from a third position to a fourth position. The forth position may include the tube arm 32 in a parked position, and the column 33 in a position intermediate between a first collapsed position and an end position. The intermediate position of the column may take on a range of values. The outer segment 17 of the column 33 may continue to retract in response to a signal received from the operator applied to the drive handle 38, as indicated by arrow 453. Alternatively, the operator may actuate a drive switch 39 located on an instrument panel or proximal to the second drive handle to initiate collapsing of the column to the end position. The operator 401 pressing the second handle 38 may cause the column motor 420 to be actuated via controller 50, which may drive down the outer segment 17 to the fully collapsed, end position. During the collapse of the column 33 to an end position, the second gas spring 418 may expand to provide additional tension on the wire rope 408. The time for the column 33 to collapse from a parked state to an end state may be a fixed duration. As an example, the time for the outer segment 17 to go from a first collapsed position to an end position may take less than 2 seconds.

During the column collapsing to the end position, a force may be applied by an operator 401 to the second handle 38. Force applied to the second handle 38 may be estimated by a second force sensor 407 contained within the handle. The force sensor 407 may then send a signal to controller 50, which may then actuate the drive motor 52, actuating drive wheels 18. The drive wheels may be operated concurrently with collapsing of the column. The speed of the drive wheels 18 may be determined, via force feedback, based on the force applied to the second handle 38. The motion of the cart 13 is indicated by arrow 454 parallel to the x axis of coordinate system 480.

FIG. 4E shows mobile imaging system 10 in a fifth position. In the fifth position, the tube arm is parked and the column is in an end position, with the second gas spring 418 fully expanded to maintain tension within the wire rope 408. The drive wheels 18 may continue to be driven at a speed determined via force feedback from the second handle 38, as described above. The motion of the cart 13 is indicated by arrow 455 parallel to the x axis of coordinate system 480.

In this way, the systems in FIGS. 1-4E provide for a system for a mobile imaging system comprising a controller storing instructions in non-transitory memory executable by the controller for: during a first condition, collapsing a column coupling a tube arm and a drive system of the mobile imaging system at a first speed while driving the drive system forward at a second speed; and during a second condition, collapsing the column at the first speed while driving the drive system forward at a third speed, the third speed higher than the second speed.

FIGS. 5A-B show a flowchart illustrating a method 500 for parking a tube arm (such as tube arm 32 of FIG. 1) and collapsing a column (such as column 33 of FIG. 1) to an end position in a mobile imaging device, such as system 10. Instructions for carrying out method 500 and the rest of the methods included herein may be executed by a controller (e.g., controller 50 shown in FIGS. 1-4E) based on instructions stored on a memory of the controller and in conjunction with signals received from sensors of the mobile imaging system, such as the sensors described above with reference to FIGS. 1-4E. The controller may employ actuators of the mobile imaging system to move the mobile imaging system, according to the methods described below. In particular, the controller may employ a drive motor (such as drive motor 52 of FIG. 2) to actuate the drive wheels (such as drive wheels 18 of FIG. 1), two separate servomotors (such as a first servomotor 210 and a second servomotor 212 of FIG. 2) to actuate tube arm motion along two independent degrees of motion, and a third servomotor (such as third servomotor 214 of FIG. 2) and a column motor (such as column motor 420 of FIG. 2) to actuate rotation and collapse of the column, respectively.

At 502, method 500 determines if the conditions have been met for parking of the tube arm. The conditions for parking may include receiving signals of force being applied to a first handle (such as first handle 66 of FIG. 1) by an operator. As described in relation to FIG. 1, the first handle may translate user movement into movement of the arm and/or column of the mobile imaging system, and may be coupled to a variety of sensors, including a first force sensor (such as a first force sensor 406 or FIG. 1), which may detect forces applied to the first handle and send signals to the controller to actuate of the tube arm and/or the column. The first force sensor may also detect forces on the tube arm due to a wire rope (such as wire rope 408 of FIGS. 4A-E) internal to the column, and may sense additional force on the tube arm due to the wire rope. Additionally, the first handle may be coupled to position sensors (such as the first position sensor 42, the second position sensor 46, and the third position sensor 48 of FIG. 1), which may send position signals corresponding to the position of the tube arm with respect to a vertical axis (such as axis 120 of FIG. 1), the radial extension of the tube arm, and the angle of rotation Φ of the column and tube arm with respect to the cart. The conditions for parking the tube arm may also include indication of completion of a scan by a user via an input to the instrument panel. The conditions for parking may further include the drive wheels being deactivated or maintaining a deactivated state, an x-ray source (such as x-ray source 15 of FIG. 1) being deactivated or maintaining a deactivated state, an imaging controller (such as imaging controller 27 of FIG. 1) being deactivated or maintaining a deactivated state, and an imaging assembly (such as imaging assembly of FIG. 1) being oriented in a start position, where the degree of rotation of the imaging assembly is zero with respect to the tube arm.

If the conditions of 502 are not met, method 500 may proceed to 501, where the tube arm may be maintained in under normal operation. Normal operation of the tube arm may include motion of the tube arm and column based on force exerted on the tube arm such as rotation, extension, and/or retraction of the tube arm as driven by motors (such as the first, second and third servomotors, and the column motor) via force feedback. Method 500 may then proceed again to 502. If the conditions for tube arm parking are met, method 500 may proceed to 504.

At 504, method 500 may proceed to drive the tube arm to a parked position based on force feedback from the first handle. The tube arm may be driven to a parked position in response to a force applied to the first handle. The driving motion may involve three separate driving mechanisms such as rotation of the column (causing corresponding rotation of the tube arm), retraction of the tube arm, and vertical downward translation of the tube arm. In other words, each of the rotation of the tube arm, the retraction of the tube arm, and the driving of the tube arm vertically may be adjusted based on a force feedback responsive to first signals received from the first force sensor coupled to the first handle of the tube arm. As an example, actuating the tube arm to the parked position may include rotating the tube arm to an origin position via rotation of the column (as discussed in relation to FIG. 4B), retracting tube arm horizontally to a fully retracted position by retracting an inner tube segment within an outer tube segment, and translating the tube arm vertically downward along the column. However, the order in which the operations take place is exemplary, and may be rearranged. For example, the tube arm may first be retracted, then the column may be rotated, and finally the tube arm may be placed in a parked position. As a further example, the rotation of the column and the retraction of the tube arm may be done in conjunction prior to being in an origin position, after which the tube arm may be driven to a parked position.

Driving the tube arm to a parked position may include, at 506, rotation of the column based on force feedback in response to a force applied to the first handle. A tangential force applied to the first handle may cause the column and tube to co-rotate with respect to the cart. The angular displacement of the column may be estimated by the third position sensor, which may then send a signal to the controller to actuate a third servomotor to drive rotation of the column at a set velocity. The set velocity may be set in accordance with the tangential force applied the first handle and the angular displacement, via the force feedback mechanism described in relation to FIG. 2. The force feedback mechanism may include determining the power applied to the third servomotor based on positional and tangential force information from the third position sensor and the first handle, respectively. The difference between the setpoint power and the actual power applied to the third servomotor may then be proportional to the tangential force applied to the first handle, as determined by a first PI controller of the first servomotor.

Driving the tube arm to a parked position may involve, at 508, retracting the tube arm based on force feedback in response to a radial force applied to the first handle. A radial inward force may cause the tube arm to retract towards the column. The position of e.g. an inner segment of the telescoping tube arm (such as inner segment 402 of FIGS. 4A-E) may be estimated by the first position sensor, which may then send a signal to the controller to actuate a first servomotor to drive the retraction of the tube arm at a fixed velocity in response to the radial force applied to the first handle and the position of the inner segment of the tube arm, via the force feedback described in relation to FIG. 2. The force feedback mechanism may include determining the power applied to the first servomotor based on positional and radial force information from the first position sensor and the first handle, respectively. The difference between the setpoint power and the actual power applied to the first servomotor may then be proportional to the radial force applied to the first handle, as determined by a second PI controller of the second servomotor.

Further, driving the tube arm to a parked position may also involve, at 510, driving the tube arm linearly downward based on force feedback in response to a vertical downward force applied to the first handle. A vertical downward force may cause the tube arm to translate vertically downwards along the vertical axis of the column. The position of the tube arm along the vertical axis in relation to the column may be estimated by the second position sensor, when may then send a signal to the controller to actuate a second servomotor to drive the tube arm linearly downward at a fixed velocity determined by the vertical force applied to the first handle, via the force feedback mechanism described in relation to FIG. 2. The force feedback mechanism may include determining the power applied to the second servomotor based on positional and vertical force information from the second position sensor and the first handle, respectively. The difference between the setpoint power and the actual power applied to the second servomotor may then be proportional to the vertical force applied to the first handle, as determined by a second PI controller of the second servomotor. Further, the tube arm may be driven even after a force applied to the first handle is ceased, e.g. due to an operator (such as operator 401 of FIGS. 4B-E) releasing the first handle. After release of the first handle, the driving may be determined by the position of the tube arm relative to the column, the vertical downward force applied to the handle upon release, and the vertical downward speed of the tube arm with respect to the column upon release.

Concurrently with driving the tube arm linearly downward to a parked position as indicated in 510, the column may be driven down at a constant speed to a first collapsed position, which may not be the fully collapsed end position, as indicated in 512, through actuation of a ball screw (such as ball screw 410 of FIGS. 4A-E) by a column motor. In other words, while actuating the tube arm to the parked position, the column may be concurrently collapsed by collapsing an outer column segment encapsulating an inner column segment until a first collapsed position is reached. The column motor may be actuated in response to a linear downward force applied to the first handle, which may cause a signal from the first force sensor to be sent to the controller, which may then actuate the column motor to drive down an outer segment of the column (such as outer segment 17 of the column of FIG. 1). The column motor may drive the ball screw via a belt drive (such as belt drive 414 of FIGS. 4A-E), which may then cause a ball nut (such as ball nut 416 of FIGS. 4A-E) to rotate, forcing the ball screw to rotate in conjunction with the rotational motion of the ball nut and translate linearly downwards. The ball screw, which may rotate relative to the column (e.g. may be fixed to the top of the interior of the outer segment of the column by a flange bearing) may then drive the outer segment of the column linearly downwards due to the linear downwards motion of the ball screw.

In conjunction with the column driving, at 514, weight compensation may be provided internally to the column as it is driven downwards via a first gas spring (such as first gas spring 412 of FIGS. 4A-E). The first gas spring may provide a counteracting force to the column to control the motion of the column as it is driven down by the column motor. The first gas spring may be fixed to the bottom of the inside of an inner segment of the column (such as inner segment 16 of FIG. 1) and the top of the inside of the outer segment of the column, and may extend if the compression force applied is less than the extension force of the first gas spring, and may otherwise compress according to the difference of the compression and extension forces. The compression forces applied to the first gas spring may include the weight of the tube arm, the force of the frame and outer segment of the column in the absence of driving, additional force of the frame and outer segment of the column in the presence of driving, and additional frictional force within the first gas spring. As an example, the force that the first gas spring may apply to the frame and outer segment of the column may be approximately (e.g. with a margin of error of 5%) 1300 N fully compressed, and 800 N fully expanded.

At 516, method 500 may check if the tube arm is in a parked condition. The tube arm being in a parked condition may include the tube arm being fastened securely to the cart via latches (such as a latch 65 fixed to the tube arm and a latch 53 fixed to the frame, as shown in FIG. 1), the tube arm being fully radially retracted, the column and tube arm having an angle of rotation $\Phi$ of 0 with respect to a longitudinal axis (such as longitudinal axis 118 of FIG. 3) of the cart, and the column being in a first collapsed position. As an example, the latches may include sensors (such as latch sensor 57 of FIG. 1), which may send a signal to the controller to indicate that the tube arm is in a parked position upon fastening of the latches. Additionally or alternatively, the parked position may be indicated by positional data for the tube arm and the column estimated by the first position sensor, the second position sensor and the third position sensor, which may be stored and recorded in the controller.

If the above conditions for tube arm parking are not met, it may be inferred that the tube arm parking is not finished. The method 500 may proceed to 503 to determine if signals are received from the second handle during tube arm parking. The mobile imaging system may include a second handle (e.g., drive handle 38) that outputs signals to the controller indicative of a desired direction of movement of the mobile imaging system. In one example, the mobile imaging system may also include a switch (such as on an instrument panel or on a smart device communicatively connected to the imaging system) that may be actuated to indicate a desire to move the imaging system to an end position and to move the system from one location to another. In response to the above signals, the controller may activate drive wheels (such as drive wheels 18 of FIG. 1), in order to move the mobile imaging system. Accordingly, if signals are received from the second handle, method 500 proceeds to 505 to activate the drive wheels. In one example, the drive wheels may be actuated at a first, constant speed. In another example, upon receiving the signals from the second handle, a speed of the drive wheels are adjusted based on the force applied on the second handle as estimated by the second force sensor contained within the second handle. While driving the drive wheels at a first speed, method 500 may then proceed to 507, where the tube arm may continue to be driven to the parked position. If no signals are received from the second handle, method 500 may directly proceed to 507 to drive the tube arm to a parked position.

If the tube arm is in a parked position, method 500 may then proceed to 518, as shown in FIG. 5B. At 518, method 500 may determine if signals are received from the second handle after the tube arm is parked. Signals received from the second handle may include force applied to the second handle by the operator in order to manually drive the cart, which may be estimated by a second force sensor coupled to the second handle (such as second force sensor 407 of FIGS. 1-4). Also, the signal for moving the mobile imaging system may come from the switch (such as on the instrument panel or on the smart device communicatively connected to the imaging system) indicating a desire to move the imaging system to an end position and to move the system from one location to another. If no signal is received from the second handle or the switch, method 500 may proceed to 509, and maintain the drive wheels in a deactivated state. The imaging system may not be moved to a different location. In one example, even if the imaging system is not being moved to a different location, the column may be actuated to a fully collapsed position via steps described in step 524 of this method. Following 509, method 500 may return.

If signals are received from a second handle or the switch, method 500 may proceed to 520 to initiate actuation of the drive wheels. The signal received may be from the application of a force on the second handle and may be estimated by the second force sensor contained within the second handle, which may then send a signal to the controller to drive the drive motor, which may actuate the drive wheels.

Motion of the drive wheels may include, at 522, adjusting speed of the drive wheels based on force feedback. The wheels may be driven, based on the force feedback, by the drive motor in response to force applied to the second handle. The force applied to the second handle may be sensed by the second force sensor contained within the handle, which may then send a signal to the controller, which may then actuate the wheels at a set speed via a force feedback loop based on the force applied to the second handle. In other words, the speed of the drive wheels is adjusted based on a force applied on the second hand-actuatable component as estimated via a force sensor, the speed proportional to the force applied. The control mechanism in the force feedback loop determining the power to be applied to the drive motor may be PI control, as described in relation to FIG. 2. A setpoint of the controller of the drive motor may be adjusted based on the output of the second force sensor contained within the second handle and a position of the drive wheels inferred based on output of a position sensor. As an example, the position sensor may be a sensor internal to the drive motor, which may continuously measure the angular position of a shaft of the drive motor. The controller of the drive motor may receive a difference between in a setpoint power and actual power delivered to the drive motor. At the PI controller, the error may be processed and/or modified (scaled) by a proportional gain. The integral of the error may be similarly processed and/or modified (scaled) by an integral gain. One of these terms or their sum is then output to a signal. The output signal of the controller may produce the final control signal to be sent to the drive motor, which may then actuate the drive wheels at a speed determined by the force applied to the second handle. In one example, the set speed for moving the drive wheels may be proportional to the force applied to the second handle. In another example, the set (second) speed for moving the drive wheels after parking of the tube arm may be higher than the first speed at which the wheels may have been actuated while parking the tube arm.

After the motion of the drive wheels is initiated in response to a force applied to the second handle, method 500 may proceed to 524, in which the column is driven to a fully collapsed, end position while the cart is in motion. In other words, actuating the column to the fully collapsed position may include collapsing the column from the first collapsed position to an end position while moving the drive system via actuation of drive wheels. In one example, the column may be collapsed at a constant speed regardless of the force applied on the second handle. In another example, the speed of collapsing of the column may be based on another force feedback responsive to second signals received from the second force sensor coupled to the second handle, the speed of collapsing directly proportional to the force applied on the second handle. Alternatively, the column may be collapsed even if motion of the cart is ceased, for example if the operator ceased applying force to the cart via the second handle.

Driving the column to a fully collapsed, end position may include, at 526, collapsing the column to a fully collapsed, end state with the column motor and ball crew. The collapsing may include actuating the column motor via force signals received by the second force sensor contained within the second handle. Additionally or alternatively, the collapsing of the column to an end position may be initiated by a drive switch (such as drive switch 39 of FIG. 1) on the second handle. The signals received from the drive handle switch may actuate the column motor via the controller. The column motor may then drive the ball nut via the belt drive, which may in turn drive the ball screw linearly downward as the ball screw is forced to rotate in conjunction with the rotational motion of the ball nut. The ball screw, which may rotate relative the column (e.g. may be attached to the top of the interior of the outer segment of the column by a flange bearing), may then drive the outer segment of the column linearly downwards in response to the linear downwards motion of the ball screw.

During collapsing of the column, as indicated in 528, the first gas spring may provide weight compensation for the column as it collapses to a fully collapsed, end position. As the column collapses to a fully collapsed, end position, the first gas spring may further compress from the state of compression maintained under the column in a first collapsed position to a further state of compression maintained under the column in a fully collapsed, end position. As an example, the first gas spring may maintain a maximal state of compression as the column collapses to a fully collapsed, end position, which may correspond to a compression force of substantially (e.g. with a variation of 5%) 1300 N as mentioned in relation to 514, or may reach some intermediate state of compression between a fully extended and fully compressed state.

Further, during collapsing of the column, at 530, method 500 may proceed to expand the second gas spring. As explained in relation to FIG. 4A, the second gas spring is fixed at one end to the top of the interior of the inner segment of the column, and may expand downwards towards the base of the interior of the column. At the other end of the second gas spring is a pulley which the wire rope may encircle. The wire rope may be fixed to the top of the interior of the inner segment of the column, may wrap around a pulley attached to the second gas spring, exit the inner segment of the column and extend upwards into the interior of the outer segment of the column. Within the interior of the outer segment of the column, the wire rope may encircle another pulley located near the top of the interior of the outer segment of the column, may finally exit the column and attach to the base of the tube arm, and may couple to the first force sensor at the base of the tube arm. As the column collapses from a parked state to a fully collapsed, end state, the wire rope may become slacken due to the relative distance between the point of attachment of the wire rope to the tube arm and the point of exit of the wire rope from the outer segment of the column decreasing. The second gas spring, which may apply a tension force to the wire rope via a pulley, may counteract the slackening tendency of the wire by expanding in response to the reduced force applied to the pulley as the wire slackens with the collapsing of the column from the parked state to the end state.

In 532, method 500 may proceed to determine if the column is in a fully collapsed, end position. This may involve a signal from a position sensor internal to the column motor to the controller that the column has reached an end range of motion in a fully collapsed state, which may then cause the controller to switch an internal column switch (such as column switch 218 of FIG. 2) to a position indicating that the column is in a fully collapsed state. The column switch 218 may indicate to the controller that the column is in a fully collapsed state, and prevent further driving of the column motor. If the column switch is not switched into the state indicating that the column is in a fully collapsed state, then method 500 may proceed to 511, where method 500 may continue to drive the column to a fully collapsed position. In one example, even if the force exerted on the second handle is removed (such as if the operator removes his hand from the second handle), the collapsing of the column may be continued until the fully collapsed state is reached. If the column is determined to be in a fully collapsed position, then method 500 may proceed to 534.

At 534, method 500 may discontinue driving the column while maintaining the motional state of the cart. As an example, the cart may be in motion due to actuation of the drive wheels in response to a force applied to the second handle. In this example, the cart may continue to remain in motion in response to force applied to the second handle while the column motor is deactivated in response to a signal received by the controller from the internal column switch indicating that the column has reached a fully collapsed, end position. As an alternate example, the cart may be at a standstill, e.g. due to an absence of force applied to the second handle, which may cause the drive wheels not to be driven by the drive motor. Following 534, method 500 may return.

Figure 6:
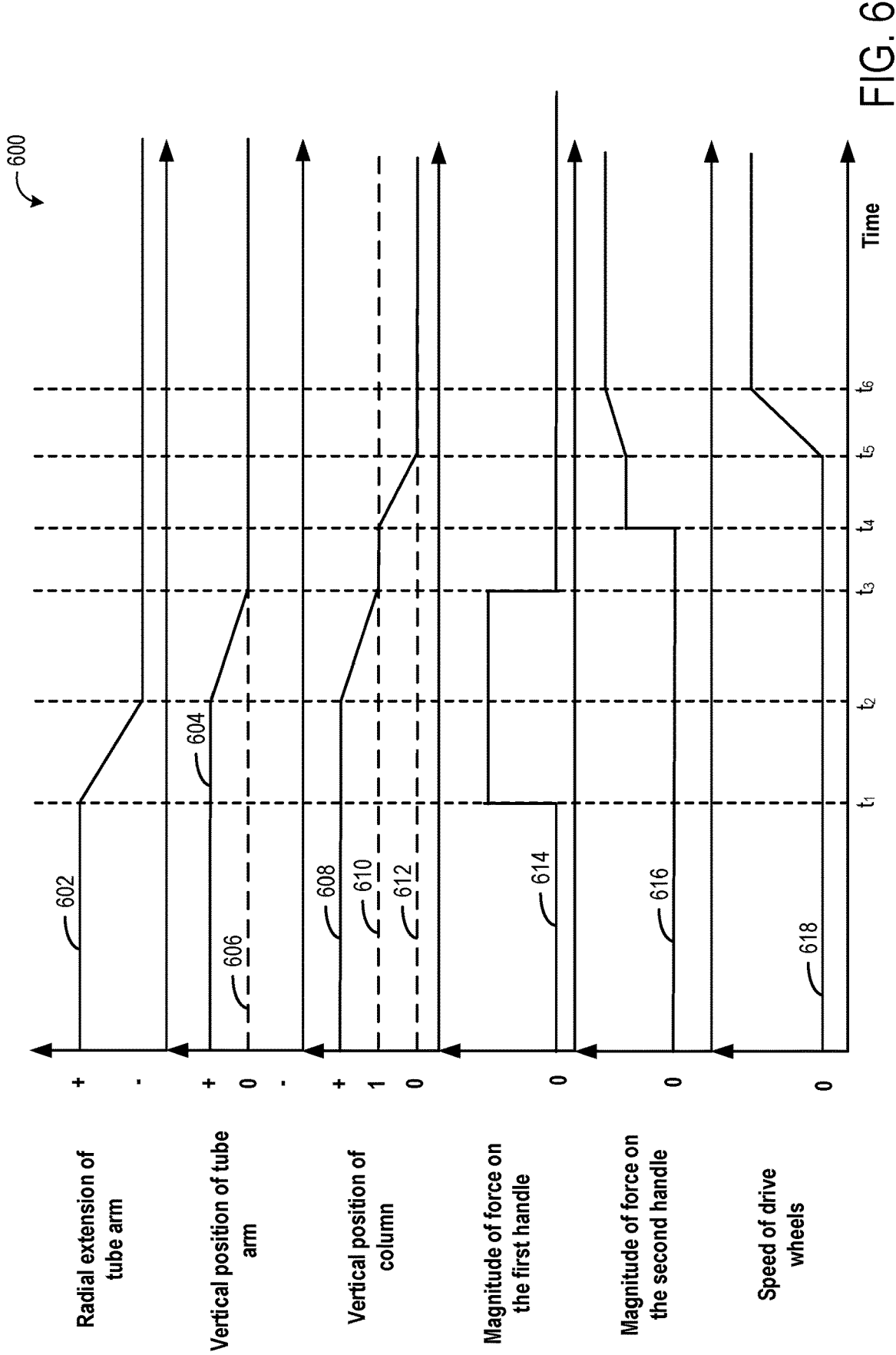
FIG. 6 shows a first example timeline for collapsing the column and driving the mobile imaging system, according to the present disclosure.

FIG. 6 shows an example timeline 600 for transitioning a mobile imaging system from an imaging configuration (such as during imaging a patient at a first location) to moving the imaging system to a different, second location. The transitioning includes parking a tube arm (such as tube arm 32, as shown in FIGS. 4A-E), and collapsing a column (such as column 33, as shown in FIGS. 1-2 and FIGS. 4A-E) to a fully collapsed position, and then actuating drive wheels (such as drive wheels 19, as shown in FIGS. 1-2 and FIGS. 4A-E) of the drive assembly by a drive motor (such as drive motor 52, as shown in FIGS. 1-2 and FIGS. 4A-E) to move the mobile imaging system from the first location to the second location. The horizontal (x-axis) denotes time and the vertical markers $t_1$-$t_6$ identify significant times in the parking, column collapse and driving of the drive wheels. In this example, the angle of rotation Φ is 0.

Timeline 600 includes plot 602 of the radial extension of the tube arm (such as the inner segment 402 of tube arm 32, as shown in FIGS. 4A-E), with the fully extended position indicated by a '+' on the y-axis, and the fully retracted position indicated by a '−' on the y-axis. The vertical position of the tube arm is indicated by plot 604, with the maximal focal point of the tube arm indicated by a '+' on the y-axis, the parked position indicated by a '0' on the y-axis, and the minimal focal point indicated by a '−' on the y-axis. Dashed line 606 indicates the parked position of the tube arm, and aligns with the '0' on the y-axis of plot 604. The plot 608 indicates the vertical position of the column, with the maximal focal point indicated by a '+' on the y-axis, the first collapsed position indicated by a '1' on the y-axis, and a fully collapsed position indicated by a '0' on the y-axis. Additionally, dashed line 610 indicates the first collapsed position of the column corresponding to the parked position of the tube arm, and is aligned with the '1' along the y-axis of plot 608, and dashed line 612 indicates the fully collapsed position of the column and is aligned with the '1' along the y-axis of plot 608. Plot 614 indicates a magnitude of force applied to a first handle (such as first handle 66 of FIGS. 1-2 and FIGS. 4A-E) coupled to the imaging assembly, with zero force indicated by a '0' along the y-axis, and plot 616 indicates a magnitude of force applied to a second handle (such as second handle 38 of FIGS. 1-2 and FIGS. 4A-E) coupled to the drive assembly with zero force indicated by a '0' along the y-axis. Plot 618 indicates a speed of the drive wheels, with stationary wheels indicated by a '0' along the y-axis.

Prior to time $t_1$, the tube arm is in an imaging configuration in which the tube arm is fully radially extended, the column is fully vertically extended to a maximal focal point, and the angle of rotation Φ is 0. At time $t_1$, in response to force exerted on the first handle to transition the tube arm to the parked position, radial retraction of the tube arm is initiated. Between time $t_1$ and $t_2$, the tube arm is radially retracted from a fully extended position to a fully retracted position. The speed of retraction of the tube arm from a fully extended position to a fully retracted position is adjusted based on based on force feedback from a first servomotor (such as first servomotor 210, as shown in FIGS. 1-2 and FIGS. 4A-E), in response to the force applied to the first handle. At time $t_2$, the tube arm is retracted to the fully retracted position.

At time $t_2$, in response to continued force applied to the first handle as shown in plot 614, parking of the tube arm is continued. Between time $t_2$ and $t_3$, each of the tube arm and the column are lowered to a parked position and a first collapsed position, as indicated by plots 604 and 608, respectively. The column and tube arm lowering is adjusted via force feedback in response to the force applied to the first handle via a column motor (such as column motor 420, as shown in FIGS. 1-2 and FIGS. 4A-E) and second servomotor (such as second servomotor 212, as shown in FIGS. 1-2 and FIGS. 4A-E) respectively. The force applied to the first handle from an operator (such as operator 401 of FIGS. 4B-E) ceases at $t_3$, as indicated in plot 614. Additionally, at $t_3$, the tube arm reaches the parked position and the column reaches the first collapsed position, as indicated by plot 604 intersecting dashed line 606 and plot 608 intersecting dashed line 610, respectively.

After the tube arm and column parking is finished, at $t_4$, the operator begins to apply the force to the second handle, as indicated in plot 616. From $t_4$ to $t_5$, in response to the force applied to the second handle, the column collapses from a first collapsed position to a fully collapsed position, as indicated by plot 608. At $t_5$, the column reaches the fully collapsed position, as indicated by plot 608 intersecting dashed line 612. After the column has reached the fully collapsed position, at $t_5$, the drive wheels are actuated by the drive motor, as shown in plot 618. A speed of rotation of the drive wheels is proportional to the force applied to the second handle via force feedback, as shown through comparison of plot 616 and plot 618.

From time $t_5$ to $t_6$, the force applied to the second handle as shown in plot 618 is continually ramped up until it reaches a steady value. Concomitantly with the ramping up of force applied to the second handle as shown in plot 616, speed of the drive wheels as shown in plot 618 is proportionally ramped up until it reaches a steady value, with the speed of the drive wheels proportional to the force applied to the second handle via force feedback. Beyond $t_6$, the drive wheels maintain a steady speed in response to the force applied to the second handle, and the cart is transported to the second location.

Figure 7:
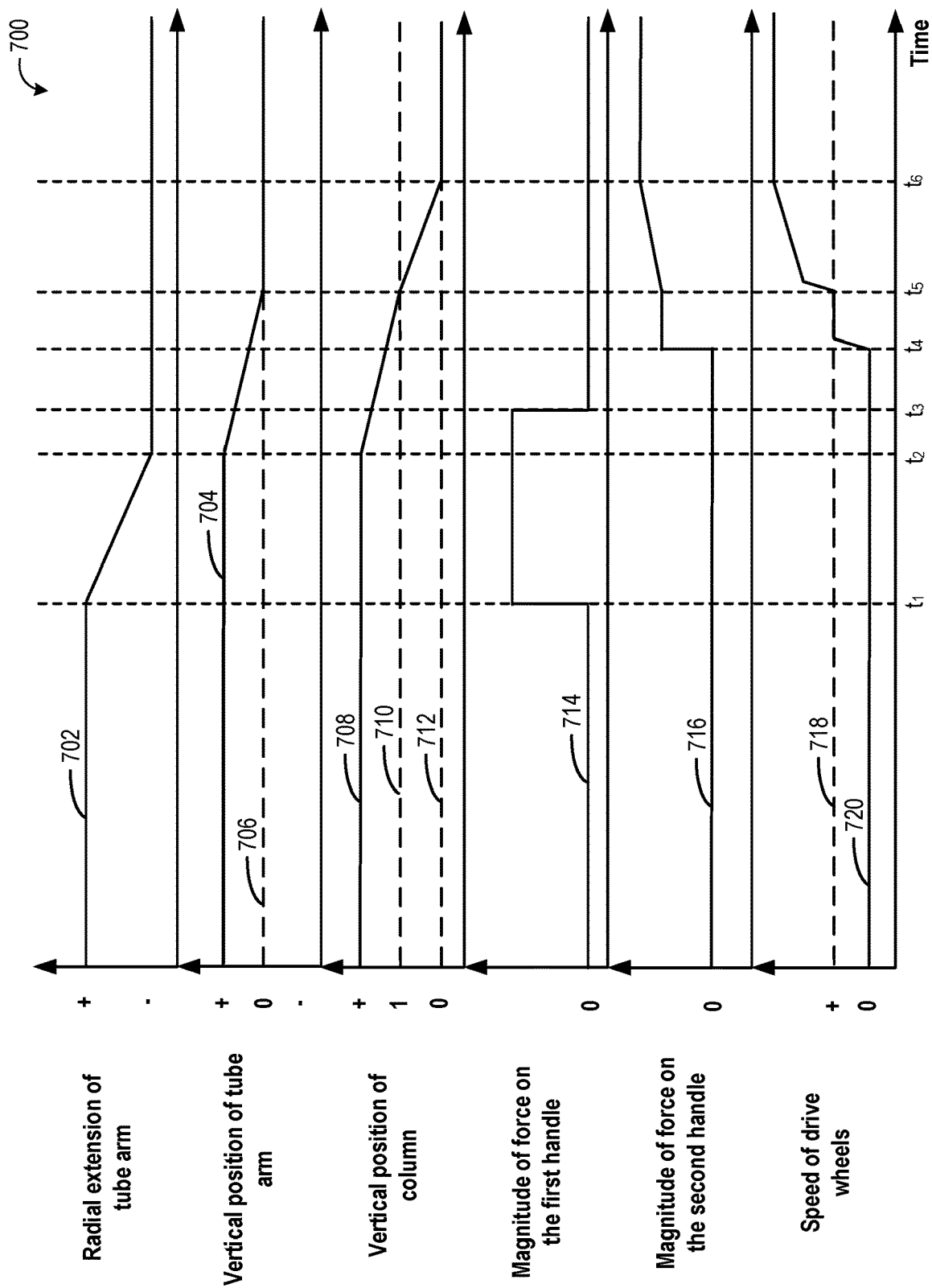
FIG. 7 shows a second example timeline for collapsing the column while driving the mobile imaging system, according to the present disclosure.

FIG. 7 shows an example timeline 700 for transitioning a mobile imaging system from an imaging configuration (such as during imaging a patient at a first location) to moving the imaging system to a different, second location. The transitioning includes parking a tube arm (such as tube arm 32, as shown in FIGS. 4A-E), and collapsing a column (such as column 33, as shown in FIGS. 1-2 and FIGS. 4A-E) to a fully collapsed position, while concomitantly actuating drive wheels (such as drive wheels 19, as shown in FIGS. 1-2 and FIGS. 4A-E) of the drive assembly by a drive motor (such as drive motor 52, as shown in FIGS. 1-2 and FIGS. 4A-E) to move the mobile imaging system from the first location to the second location. The horizontal (x-axis) denotes time and the vertical markers $t_1$-$t_6$ identify significant times in the parking, column collapse and driving of the drive wheels. In this example, the angle of rotation Φ is 0. Example timeline 700 illustrates the reduction in time in going from an imaging configuration to transporting the mobile imaging system when the parking of the tube arm and collapse of the column are enacted concomitantly with driving the mobile imaging system, as compared to the example timeline 600 of FIG. 6.

Timeline 700 includes plot 702 of the radial extension of the tube arm (such as the inner segment 402 of tube arm 32, as shown in FIGS. 4A-E), with the fully extended position indicated by a '+' on the y-axis, and the fully retracted position indicated by a '−' on the y-axis. The vertical position of the tube arm is indicated by plot 704, with the maximal focal point of the tube arm indicated by a '+' on the y-axis, the parked position indicated by a '0' on the y-axis, and the minimal focal point indicated by a '−' on the y-axis. Dashed line 706 indicates the parked position of the tube arm, and aligns with the '0' on the y-axis of plot 704. The plot 708 indicates the vertical position of the column, with the maximal focal point indicated by a '+' on the y-axis, the first collapsed position indicated by a '1' on the y-axis, and a fully collapsed position indicated by a '0' on the y-axis. Additionally, dashed line 710 indicates the first collapsed position of the column corresponding to the parked position of the tube arm, and is aligned with the '1' along the y-axis of plot 708, and dashed line 712 indicates the fully collapsed position of the column and is aligned with the '1' along the y-axis of plot 708. Plot 714 indicates a magnitude of force applied to a first handle (such as first handle 66, as shown in FIGS. 1-2 and FIGS. 4A-E) coupled to the imaging assembly, with zero force indicated by a '0' along the y-axis, and plot 716 indicates a magnitude of force applied to a second handle (such as second handle 38, as shown in FIGS. 1-2 and FIGS. 4A-E) coupled to the drive assembly with zero force indicated by a '0' along the y-axis. Plot 720 is of the speed of the drive wheels, with stationary wheels indicated by a '0' along the y-axis. Dashed line 718 indicates a first threshold speed of the drive wheels, and aligns with the '+' along the y-axis of plot 720. The first threshold speed is a pre-calibrated speed at which the drive wheels may be rotated upon exertion of force on the second handle during parking of the tube arm.

Prior to time $t_1$, the tube arm is in an imaging configuration in which the tube arm is fully radially extended, the column is fully vertically extended to a maximal focal point, and the angle of rotation Φ is 0. At time $t_1$, in response to force exerted on the first handle to transition the tube arm to the parked position, radial retraction of the tube arm is initiated. From $t_1$ to $t_2$, the tube arm position, as shown in plot 702, is radially retracted from a fully extended position to a fully retracted position. The speed of retraction of the tube arm from a fully extended position to a fully retracted position is adjusted based on based on force feedback from a first servomotor (such as first servomotor 210, as shown in of FIGS. 1-2 and FIGS. 4A-E), in response to the force applied to the first handle. At time $t_2$, the tube arm is retracted to the fully retracted position.

At time $t_2$, in response to continued force applied to the first handle as shown in plot 714, parking of the tube arm is continued. Between time $t_2$ and $t_3$, each of the tube arm and the column are lowered to a parked position and a first collapsed position, as indicated by plots 704 and 708, respectively. The column and tube arm lowering is adjusted in response to the force applied to the first handle via a column motor (such as column motor 420, as shown in FIGS. 1-2 and FIGS. 4A-E) and second servomotor (such as second servomotor 212, as shown in FIGS. 1-2 and FIGS. 4A-E) respectively via force feedback, with the downward speed of the tube arm and the column proportional to the force applied to the first handle. At $t_3$, an operator (such as operator 401 of FIGS. 4B-E) ceases to apply force to the first handle as shown in plot 714, and the column and tube arm continue to translate linearly downward at the same speed.

While the tube arm and column parking is in progress, such as while the tube arm and column continue to linearly translate downward proportionally to the force applied to the first handle, at $t_4$, the operator applies a force to the second handle, as shown in plot 716. From $t_4$ to $t_5$, in response to the force applied to the second handle, the drive wheels ramp up to the first threshold speed, as shown in plot 720. Since parking of the tube arm is in progress, between time $t_4$ and $t_5$, regardless of the force applied to the second handle, the speed of the drive wheels is maintained at the first threshold speed, as indicated by plot 720 intersecting dashed line 718.

At $t_5$, the tube arm reaches the parked position and the column reaches the first collapsed position, as indicated by plot 704 intersecting dashed line 706 and plot 708 intersecting dashed line 710, respectively. After the first collapsed position has reached, between $t_5$ to $t_6$, in response to continued application of force to the second handle, the column continues to collapse to a fully collapsed position at a higher speed than during the collapse from the maximal focal point to the first collapsed position. The increase in the speed of collapse of the column is indicated in plot 708. In alternate examples, the collapsing of the column is carried out at a constant speed from the maximal focal point to the fully collapsed (final) position. Additionally, upon completion of parking, at $t_5$, the speed of the drive wheels is increased from a first threshold speed to a second speed, as shown in plot 720, is the second speed being proportional to the force applied the second handle.

From time $t_5$ to $t_6$, the force applied to the second handle as shown in plot 716 is continually ramped up until it reaches a steady value. Concomitantly with the ramping up of force applied to the second handle as shown in plot 716, speed of the drive wheels as shown in plot 720 is proportionally ramped up until it reaches a steady value, with the speed of the drive wheels proportional to the force applied to the second handle via force feedback. Beyond $t_6$, the drive wheels maintain a steady speed in response to the force applied to the second handle, and the cart is in a transport mode. In this way, in the example shown in FIG. 7, by starting to drive the drive wheels while the tube arm is being parked and the column is being collapsed, the time for transitioning the mobile imaging system from the imaging configuration at a first location to a different, second imaging location is reduced. The time taken for the imaging assembly to reach the second location would be shorter for the example shown in FIG. 7 relative to the time taken in the example shown in FIG. 6 where the drive wheels could be actuated after the tube arm and the column reached their respective fully retracted positions.

In this way, for a mobile imaging system including a radiation source coupled to a drive system via a tube arm and a column, responsive to user manipulation of a first hand-actuatable component the tube arm may be actuated to a parked position, and then responsive to user manipulation of a second hand-actuatable component, the column may be actuated to a fully collapsed position while moving the drive system.

A technical effect of a mobile imaging system with mechanisms for collapsing a column concomitantly with drive motion of the mobile imaging system, is to reduce the time interval during the transition from an imaging configuration of the mobile imaging system to a transport configuration of the mobile imaging system. Overall, by reducing the time between two scans at two different locations using the imaging assembly, workflow in a busy clinic/hospital may be expedited.

An example provides for a method for a mobile imaging system, including upon conditions being met for moving the mobile imaging system, collapsing a column coupling an imaging assembly to a drive system while concomitantly moving the drive system. In a first example of the method, the imaging assembly is coupled to the column via a rotatable and extendable tube arm, the column coupling the tube arm to the drive system. In a second example of the method, which optionally includes the first example, the conditions for moving the mobile imaging system includes exertion of force on a second handle coupled to the drive system or actuation of a switch by an user during or after parking the tube arm. In a third example of the method, which optionally includes one or both of the first and second examples, parking of the tube arm is initiated by exerting force on a first handle coupled to the imaging assembly. In a fourth example of the method, which optionally includes one or more or each of the first through third examples, the parking of the tube arm includes rotation of the tube arm to an origin position, retraction of the tube arm towards the column to a fully retracted position, and driving the tube arm vertically downwards along the column. In a fifth example of the method, which optionally includes one or more or each of the first through fourth examples, each of the rotation of the tube arm, the retraction of the tube arm, and the driving of the tube arm vertically is adjusted based on a force feedback responsive to first signals received from a first force sensor coupled to the first handle or the tube arm. In a sixth example of the method, which optionally includes one or more or each of the first through fifth examples, the retraction of the tube arm is further based on a first input from a first position sensor coupled to the column indicating a radial position of the tube arm, wherein the driving of the tube arm vertically is further based on a second input from a second position sensor coupled to the tube arm indicating a vertical position of the tube arm relative to the column, and wherein the rotation of the tube arm is further based on a third input from a third position sensor coupled to the column indicating an angular displacement of the column and the tube arm relative to the origin position. In a seventh example of the method, which optionally includes one or more or each of the first through sixth examples, collapsing the column includes collapsing the column to a fully collapsed position, a speed of collapsing of the column based on another force feedback responsive to second signals received from a second force sensor coupled to the second handle. In an eighth example of the method, which optionally includes one or more or each of the first through seventh examples, during collapsing the column, a first gas spring housed within the column is compressed to provide weight compensation while a second gas spring housed within the column is expanded to maintain tension in a wire rope. In a ninth example of the method, which optionally includes one or more or each of the first through eighth examples, moving the drive system includes actuating a set of drive wheels coupled to the drive system with a speed of the drive wheels adjusted based on the second signals received from a second force sensor coupled to the second handle.

An example provides for a method for a mobile imaging system including a radiation source coupled to a drive system via a tube arm and a column, the method including responsive to user manipulation of a first hand-actuatable component, actuating the tube arm to a parked position, and then responsive to user manipulation of a second hand-actuatable component, actuating the column to a fully collapsed position while moving the drive system. In a first example of the method, actuating the tube arm to the parked position includes rotating the tube arm to an origin position via rotation of the column, retracting tube arm horizontally to a fully retracted position by retracting an inner tube segment within an outer tube segment, and translating the tube arm vertically downward along the column. In a second example of the method, which optionally includes the first example, user manipulation of the first hand-actuatable component includes application of force on the first hand-actuatable component to initiate the parking of the tube arm and then releasing the first hand-actuatable component. In a third example of the method, which optionally includes one or both of the first and second examples, while actuating the tube arm to the parked position, collapsing the column by collapsing an inner column segment within an inner column segment until a first collapsed position is reached. In a fourth example of the method, which optionally includes one or more or each of the first through third examples, actuating the column to the fully collapsed position includes collapsing the column from the first collapsed position to an end position while moving the drive system via actuation of drive wheels. In a fifth example of the method, which optionally includes one or more or each of the first through fourth examples, a speed of the drive wheels is adjusted based on a force applied on the second hand-actuatable component as estimated via a force sensor, the speed proportional to the force applied.

An example provides for a system for a mobile imaging system comprising a controller storing instructions in non-transitory memory executable by the controller to: during a first condition, collapse a column coupling a tube arm and the drive system of the imaging system at a first speed while driving the drive system forward at a second speed, and during a second condition, collapse the column at the first speed while driving the drive system forward at a third speed, the third speed higher than the second speed. In a first example of the system, the first condition includes receiving a second signal from a second handle while the tube arm is being actuated from a scan position to a parked position in response to a first signal received at a first handle, and the second condition includes receiving the second signal from the second handle after the tube arm reaching the parked position. In a second example of the system, which optionally includes the first example, the parked position includes the tube arm being in a fully retracted position, aligned along the drive system, and translated to a lowest point of the tube arm along the column, and the column being retracted to a first position, and wherein upon receiving the second signal, the column is collapsed to an end, fully retracted position. In a third example of the system, which optionally includes one or both of the first and second examples, the second signal includes an estimation of force applied on the second handle, and the fourth speed is adjusted based on the estimation of the force applied on the second handle and a position of the drive system.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a mobile imaging system, comprising:
   upon conditions being met for moving the mobile imaging system,
   collapsing a column coupling an imaging assembly to a drive system while concomitantly moving the drive system.

2. The method of claim 1, wherein the imaging assembly is coupled to the column via a rotatable and extendable tube arm, the column coupling the tube arm to the drive system.

3. The method for claim 1, wherein the conditions for moving the mobile imaging system includes exertion of force on a second handle coupled to the drive system or actuation of a switch by a user during or after parking a tube arm.

4. The method of claim 3, wherein parking of the tube arm is initiated by exerting force on a first handle coupled to the imaging assembly.

5. The method of claim 4, wherein the parking of the tube arm includes rotation of the tube arm to an origin position, retraction of the tube arm towards the column to a fully retracted position, and driving the tube arm vertically downwards along the column.

6. The method of claim 5, wherein each of the rotation of the tube arm, the retraction of the tube arm, and the driving of the tube arm vertically is adjusted based on a force feedback responsive to first signals received from a first force sensor coupled to the first handle or the tube arm.

7. The method of claim 6, wherein the retraction of the tube arm is further based on a first input from a first position sensor coupled to the column indicating a radial position of the tube arm, wherein the driving of the tube arm vertically is further based on a second input from a second position sensor coupled to the tube arm indicating a vertical position of the tube arm relative to the column, and wherein the rotation of the tube arm is further based on a third input from a third position sensor coupled to the column indicating an angular displacement of the column and the tube arm relative to the origin position.

8. The method of claim 3, wherein collapsing the column includes collapsing the column to a fully collapsed position, a speed of collapsing of the column based on another force feedback responsive to second signals received from a second force sensor coupled to the second handle.

9. The method of claim 8, wherein during collapsing the column, a first gas spring housed within the column is compressed to provide weight compensation while a second gas spring housed within the column is expanded to maintain tension in a wire rope.

10. The method of claim 8, wherein moving the drive system includes actuating a set of drive wheels coupled to the drive system with a speed of the drive wheels adjusted based on the second signals received from a second force sensor coupled to the second handle.

11. A method for a mobile imaging system including a radiation source coupled to a drive system via a tube arm and a column, the method comprising:
    responsive to user manipulation of a first hand-actuatable component, actuating the tube arm to a parked position; and
    then responsive to user manipulation of a second hand-actuatable component, actuating the column to a fully collapsed position while moving the drive system.

12. The method of claim 11, wherein actuating the tube arm to the parked position includes rotating the tube arm to an origin position via rotation of the column, retracting the tube arm horizontally to a fully retracted position by retracting an inner tube segment within an outer tube segment, and translating the tube arm vertically downward along the column.

13. The method of claim 12, wherein user manipulation of the first hand-actuatable component includes application of force on the first hand-actuatable component to initiate parking of the tube arm and then releasing the first hand-actuatable component.

14. The method of claim 11, further comprising, while actuating the tube arm to the parked position, collapsing the column by collapsing an outer column segment encapsulating an inner column segment until a first collapsed position is reached.

15. The method of claim 11, wherein actuating the column to the fully collapsed position includes collapsing the column from a first collapsed position to an end position while moving the drive system via actuation of drive wheels.

16. The method of claim 15, wherein a speed of the drive wheels is adjusted based on a force applied on the second hand-actuatable component as estimated via a force sensor, the speed proportional to the force applied.

17. A system for a mobile imaging system comprises a controller storing instructions in non-transitory memory executable by a controller to:
    during a first condition, collapsing a column coupling a tube arm and a drive system of the mobile imaging system at a first speed while driving the drive system forward at a second speed; and
    during a second condition, collapsing the column at the first speed while driving the drive system forward at a third speed, the third speed higher than the second speed.

18. The system of claim 17, wherein the first condition includes receiving a second signal from a second handle while the tube arm is being actuated from a scan position to a parked position in response to a first signal received at a first handle, and the second condition includes receiving the second signal from the second handle after the tube arm reaching the parked position.

19. The system of claim 18, wherein the parked position includes the tube arm being in a fully retracted position, aligned along the drive system, and translated to a lowest point of the tube arm along the column, and the column being retracted to a first position, and wherein upon receiving the second signal, the column is collapsed to an end, fully retracted position.

20. The system of claim 18, wherein the second signal includes an estimation of force applied on the second handle, and the third speed is adjusted based on the estimation of the force applied on the second handle and a position of the drive system.

* * * * *